United States Patent
Seki

(10) Patent No.: US 12,018,007 B2
(45) Date of Patent: Jun. 25, 2024

(54) METHOD FOR MANUFACTURING DIARYLMETHANE COMPOUND

(71) Applicant: Tokuyama Corporation, Shunan (JP)

(72) Inventor: Masahiko Seki, Yamaguchi (JP)

(73) Assignee: Tokuyama Corporation, Yamaguchi (JP)

( * ) Notice: Subject to any disclaimer, the term of this patent is extended or adjusted under 35 U.S.C. 154(b) by 827 days.

(21) Appl. No.: 17/058,908

(22) PCT Filed: May 30, 2019

(86) PCT No.: PCT/JP2019/021460
§ 371 (c)(1),
(2) Date: Nov. 25, 2020

(87) PCT Pub. No.: WO2019/230864
PCT Pub. Date: Dec. 5, 2019

(65) Prior Publication Data
US 2021/0198231 A1  Jul. 1, 2021

(30) Foreign Application Priority Data

May 31, 2018 (JP) .................. 2018-104250
May 31, 2018 (JP) .................. 2018-104251

(51) Int. Cl.
*C07D 333/12* (2006.01)
*B01J 27/135* (2006.01)
*B01J 31/02* (2006.01)

(52) U.S. Cl.
CPC .......... *C07D 333/12* (2013.01); *B01J 27/135* (2013.01); *B01J 31/0231* (2013.01); *B01J 2231/643* (2013.01); *B01J 2531/46* (2013.01)

(58) Field of Classification Search
CPC ... C07D 333/12; B01J 27/135; B01J 31/0231; B01J 2231/643; B01J 2531/46
See application file for complete search history.

(56) References Cited

U.S. PATENT DOCUMENTS

| 4,172,082 A | 10/1979 | Moore |
| 2010/0204487 A1 | 8/2010 | Davies et al. |
| 2017/0044129 A1 | 2/2017 | Liao et al. |

FOREIGN PATENT DOCUMENTS

| CN | 103570671 A | 2/2014 |
| CN | 104086523 A | 10/2014 |
| CN | 105272960 A | 1/2016 |
| GB | 1 398 683 | 6/1975 |
| JP | 48-097852 | 12/1973 |
| JP | 53-141265 | 12/1978 |
| JP | 02-311442 A | 12/1990 |
| JP | 2010-180143 A | 8/2010 |
| JP | 2010-180173 A | 8/2010 |
| JP | 2010-535765 A | 11/2010 |
| JP | 2012-505858 A | 3/2012 |
| WO | 2010/043682 | * 4/2010 |
| WO | WO-2010/043682 A2 | 4/2010 |
| WO | 2016/178148 | * 11/2016 |
| WO | WO-2016/178148 A1 | 11/2016 |
| WO | 2017/130217 | * 8/2017 |
| WO | WO-2017/130217 A1 | 8/2017 |

OTHER PUBLICATIONS

Office Action dated Dec. 15, 2022 in IN 202017055488.
Bokor et al., "C-Glycopyranosyl Arenes and Hetarenes: Synthetic Methods and Bioactivity Focused on Antidiabetic Potential," Chemical Reviews, 2017, 117:1687-1764.
International Search Report dated Aug. 13, 2019 in PCT/JP2019/021460.
Liang-Zhen et al., "Reduction of 4-trans-alkylcyclohexylcarboxylic Acid and its Ester by NaBH4/Lewis Acid under Room Temperature," Chinese Journal of Liquid Crystals and Displays, Dec. 2007, 22(6):652-656, with English abstract.
Office Action dated Nov. 8, 2022 in CN 201980032724.5, with English machine translation.
Office Action dated Oct. 28, 2022 in JP 2019-101121, with machine English translation.
Office Action dated Jun. 24, 2022 in TW 108118721, with English translation.

(Continued)

*Primary Examiner* — D Margaret M Seaman
(74) *Attorney, Agent, or Firm* — Foley & Lardner LLP

(57) ABSTRACT

An object is to provide a method for producing a compound which is useful as a synthetic intermediate for an active pharmaceutical ingredient of an antidiabetic drug or the like in an industrially inexpensive and efficient manner, and the present invention can achieve the object by reducing a compound (2) represented by the following formula (2):

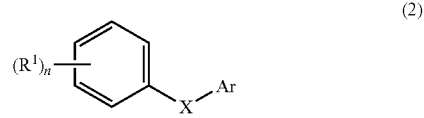

(2)

wherein $R_1$, Ar, n and X are as mentioned herein in the presence of a titanium compound by using a reducing agent to produce a compound (1) represented by the following formula (1):

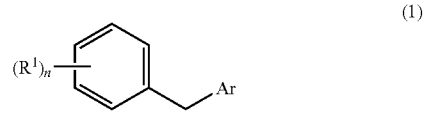

(1)

wherein $R_1$, Ar and n are the same as defined above.

10 Claims, No Drawings

(56) References Cited

OTHER PUBLICATIONS

Brown et al., "A New Powerful Reducing Agent-Sodium Borohydride in the Presence of Aluminum Chloride and Other Polyvalent Metal Halides," Journal of American Chemical Society, Jun. 1, 1956, 78(11):2582-2588.

Office Action dated Aug. 25, 2023 in KR 10-2020-7032699, with English translation.

* cited by examiner

METHOD FOR MANUFACTURING DIARYLMETHANE COMPOUND

CROSS-REFERENCE TO RELATED APPLICATIONS

This application is the U.S. National Stage of PCT/JP2019/021460, filed May 30, 2019, which claims priority to JP 2018-104250, filed May 31, 2018 and JP 2018-104251, filed May 31, 2018.

BACKGROUND OF THE INVENTION

Field of the Invention

The present invention relates to a method for producing a compound (for example, a diarylmethane compound) which is useful as a synthetic intermediate for an active pharmaceutical ingredient of an antidiabetic drug or the like. Particularly, the present invention relates to a method for producing a compound (for example, a diarylmethane compound) which is useful as a synthetic intermediate for an active pharmaceutical ingredient of an antidiabetic drug or the like in an industrially inexpensive and efficient manner.

Background Art

A diarylmethane compound is a compound which is useful as a synthetic intermediate for an active pharmaceutical ingredient of an antidiabetic drug or the like (see Non Patent Document 1). As a method for producing canagliflozin, which is one of antidiabetic drugs, there has been known a method for producing canagliflozin (8) through the following synthetic route (see Patent Document 1). In the following synthetic route, a diarylmethane compound (4) is synthesized by the reduction reaction of a diarylketone compound (3). Patent Document 1 also mentions a method for producing a diarylmethane compound by the reduction reaction of diarylalcohol.

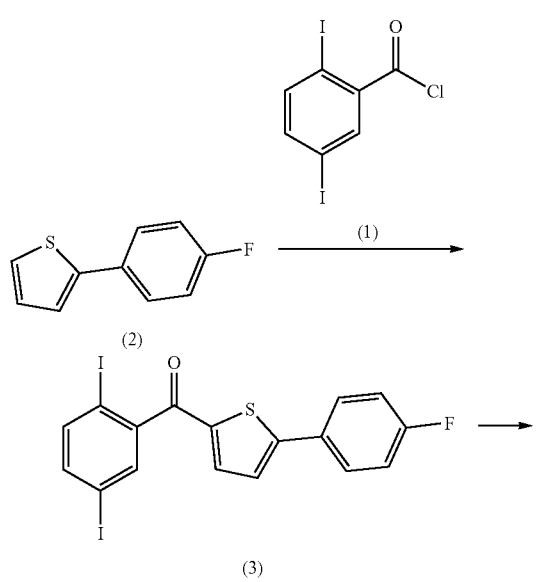

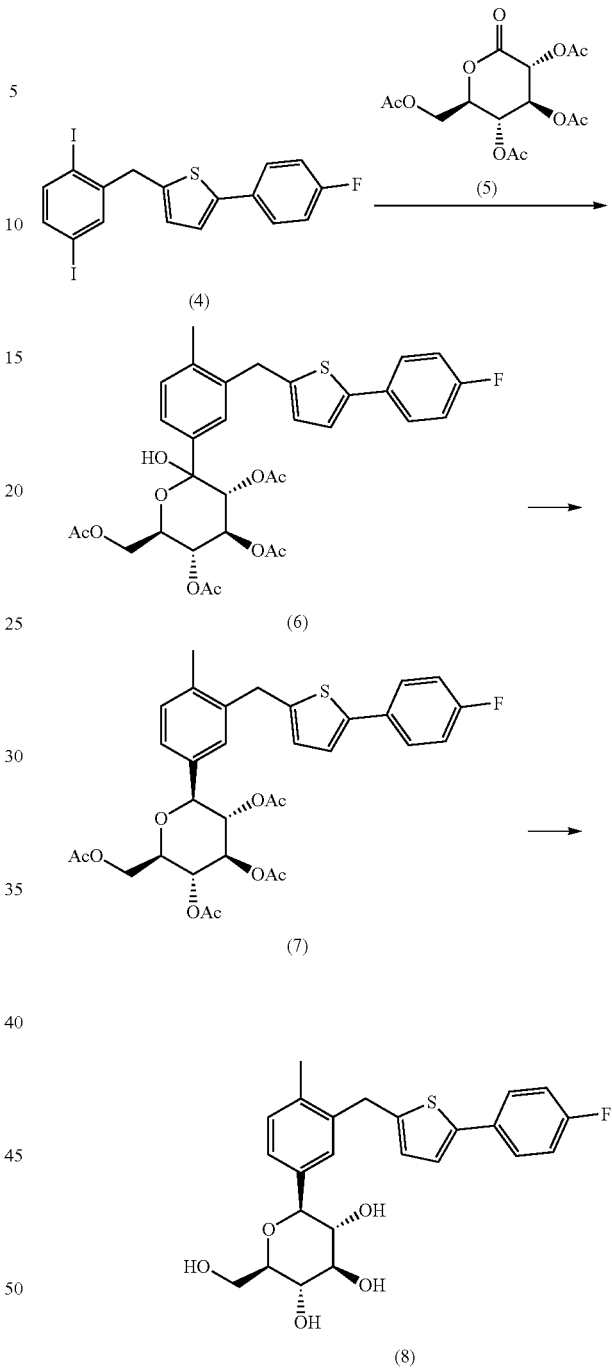

With respect to the above reduction reaction of the diarylketone compound (3) or diarylalcohol, Patent Document 1 mentions a method which uses silane compounds such as alkylsilane and alkylsiloxane in the presence of Lewis acids such as $BF_3 \cdot Et_2O$, $BF_3 \cdot THF$, $AlCl_3$, $ZnCl_2$ and $FeCl_3$. In addition, Patent Document 2 mentions a method for acting hydrogen gas in the coexistence of a metal catalyst such as palladium, and a method which uses a borohydride salt and aluminum chloride or trifluoromethanesulfonic acid. Furthermore, Patent Document 3 mentions a production method which uses an alkali metal borohydride and trifluoroacetic acid or $BF_3 \cdot Et_2O$.

PRIOR ART DOCUMENT

Patent Document

Patent Document 1: JP 2012-505858 A
Patent Document 2: JP 2010-180143 A
Patent Document 3: CN 105272960 A

Non Patent Document

Non Patent Document 1: Cem. Rev, 2017, 117, 1687-1764

SUMMARY OF THE INVENTION

Problems to be Solved by the Invention

However, all of silane compounds such as alkylsilane and alkylsiloxane, reducing agents such as trifluoroboron, trifluoromethanesulfonic acid and trifluoroacetic acid are expensive, and still had problems in terms of industrially inexpensive production. In addition, all of Lewis acids such as $AlCl_3$, $ZnCl_2$ and $FeCl_3$ are insoluble and had problems in terms of handling.

Thus, the above methods had problems with production on an industrially large scale.

Therefore, an object of the present invention to provide a method for producing a compound (for example, a diarylmethane compound) which is useful as a synthetic intermediate for an active pharmaceutical ingredient of an antidiabetic drug or the like in an industrially inexpensive and efficient manner.

Solution to the Problems

The present inventors have intensively studied to solve the above problems. The present inventors have studied on reducing agents which reduce diarylketone compounds or diarylalcohol and additives which accelerate a reduction reaction, and have found that when a reduction reaction is performed in the presence of a titanium compound by using a reducing agent, the reaction effectively proceeds. In addition, the present inventors have found that the titanium compound is industrially extremely inexpensive, readily soluble in the above reaction system, and easy to handle in the reaction, thus completing the present invention.

The present inventions include the following inventions.

[1] A method for producing a compound (1) represented by the following formula (1):

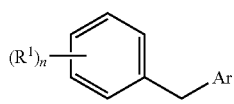

(1)

wherein
$R^1$ each independently is a group selected from a halogen atom, an amino group, a substituted or unsubstituted $C_{1-6}$ alkyl group, a substituted or unsubstituted $C_{1-6}$ alkoxy group, a substituted or unsubstituted $C_{2-6}$ heteroalkyl group, a substituted or unsubstituted $C_{2-6}$ heteroalkoxy group, a substituted or unsubstituted $C_{1-6}$ monoalkylamino group, a substituted or unsubstituted $C_{2-6}$ dialkylamino group, a substituted or unsubstituted alicyclic group, a substituted or unsubstituted alicyclic oxy group, a substituted or unsubstituted aliphatic heterocyclic group, a substituted or unsubstituted aliphatic heterocyclic oxy group, a substituted or unsubstituted phenyl group, a substituted or unsubstituted phenyloxy group, a substituted or unsubstituted $C_{7-10}$ phenylalkyl group and a substituted or unsubstituted $C_{7-10}$ phenylalkyloxy group, n is an integer of 0 to 5, Ar is a group selected from a substituted or unsubstituted aromatic ring group and a substituted or unsubstituted aromatic heterocyclic group, the method comprising the following steps (a) and (b):

(a) a step of providing a compound (2) represented by the following formula (2):

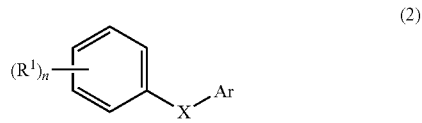

(2)

wherein
$R^1$, Ar and n are the same as defined above,
X is a group selected from —C(=O)—, —CH(—OH)— and —CH(—OR²)—,
$R^2$ is a group selected from a substituted or unsubstituted $C_{1-6}$ alkyl group and a substituted or unsubstituted $C_{7-10}$ phenylalkyl group; and (b) a step of reducing the compound (2) in the presence of a titanium compound by using a reducing agent to produce the compound (1).

[2] The production method according to [1], wherein the titanium compound used in the step (b) is a titanium salt represented by the following formula (3):

$$TiR^3{}_r(OR^4)_s \quad (3)$$

wherein
$R^3$ is a halogen atom,
$R^4$ is a substituted or unsubstituted $C_{1-6}$ alkyl group,
r and s are integers of 0 to 4 satisfying r+s=3 or 4, or a solvate thereof.

[3] The production method according to [1] or [2], wherein the reducing agent used in the step (b) is an alkali metal borohydride salt.

[4] The production method according to any one of [1] to [3], wherein in the step (b), the titanium compound and the reducing agent are added to a solvent to react the reducing agent with the titanium compound at 20 to 120° C., followed by addition of the compound (2) to the solvent.

[5] The production method according to any one of [1] to [4], wherein
the compound (2) is a compound (2-1) represented by the following formula (2-1):

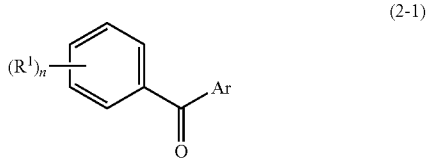

(2-1)

wherein $R^1$, Ar and n are the same as defined above, and the step (a) comprises a step of reacting a compound (4) represented by the following formula (4):

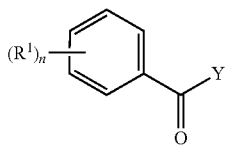

wherein R¹ and n are the same as defined above, and Y is a halogen atom,
with a compound (5) represented by the following formula (5):

H—Ar   (5)

wherein Ar is the same as defined above, in the presence of a titanium compound to produce the compound (2-1).

[6] The production method according to [5], wherein the titanium compound used in the step (a) is the titanium salt represented by formula (3) or a solvate thereof.

[7] The production method according to any one of [1] to [6], wherein Ar is a group represented by the following formula (Ar-1), (Ar-2) or (Ar-3):

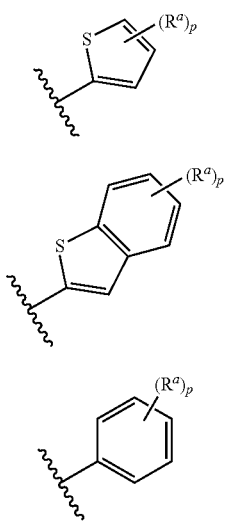

wherein
$R^a$ each independently is a halogen atom, an amino group, a substituted or unsubstituted $C_{1-6}$ alkyl group, a substituted or unsubstituted $C_{1-6}$ alkoxy group, a substituted or unsubstituted $C_{2-6}$ heteroalkyl group, a substituted or unsubstituted $C_{2-6}$ heteroalkoxy group, a substituted or unsubstituted $C_{1-6}$ monoalkylamino group, a substituted or unsubstituted $C_{2-6}$ dialkylamino group, a substituted or unsubstituted alicyclic group, a substituted or unsubstituted alicyclic oxy group, a substituted or unsubstituted aliphatic heterocyclic group, a substituted or unsubstituted aliphatic heterocyclic oxy group, a substituted or unsubstituted phenyl group, a substituted or unsubstituted phenyloxy group, a substituted or unsubstituted $C_{7-10}$ phenylalkyl group and a substituted or unsubstituted $C_{7-10}$ phenylalkyloxy group, and
p is an integer of 0 to 5.

Advantageous Effects of the Invention

According to the present invention, it is possible to efficiency produce the compound (1) in a high yield by using a titanium compound in place of trifluoromethanesulfonic acid and trifluoroacetic acid, which are expensive reagents, and aluminum chloride, etc., which had difficulty in handling. Furthermore, since a titanium compound is readily soluble in the reaction system, operation after the reaction is simple, and it is possible to produce the compound (2-1) industrially efficiently.

DETAILED DESCRIPTION OF THE INVENTION

Hereinafter, the present invention will be described. When two or more embodiments among embodiments mentioned herein can be combined, such a combination is also included in the present invention.

Description of Terms

Hereinafter, the terms used herein will be described. The following descriptions are applied throughout the present specification unless otherwise specified.

Halogen Atom

"Halogen atom" means a fluorine atom, a chlorine atom, a bromine atom or an iodine atom.

Substituted or Unsubstituted $C_{1-6}$ Alkyl Group

"Substituted or unsubstituted $C_{1-6}$ alkyl group" means a $C_{1-6}$ alkyl group or a $C_{1-6}$ alkyl group having one or more substituents.

"$C_{1-6}$ alkyl group" means a linear alkyl group having 1 to 6 carbon atoms or a branched alkyl group having 3 to 6 carbon atoms. The number of carbon atoms of the linear alkyl group is preferably 1 to 5, more preferably 1 to 4, still more preferably 1 to 3, and yet more preferably 1 or 2. The number of carbon atoms of the branched alkyl group is preferably 3 to 5, and more preferably 3 or 4. Examples of the $C_{1-6}$ alkyl group include a methyl group, an ethyl group, a propyl group, an isopropyl group, an n-butyl group, an isobutyl group, a sec-butyl group, a tert-butyl group and the like.

In the $C_{1-6}$ alkyl group having one or more substituents, one or more substituents each are substituted for a hydrogen atom of the $C_{1-6}$ alkyl group. The number of substituents which may be possessed by the $C_{1-6}$ alkyl group is preferably 1 to 3, and more preferably 1 or 2. When the number of substituents is 2 or more, two or more substituents may be the same or different from each other. One or more substituents which may be possessed by the $C_{1-6}$ alkyl group each independently can be selected from a halogen atom.

Substituted or Unsubstituted $C_{1-6}$ Alkoxy Group

"Substituted or unsubstituted $C_{1-6}$ alkoxy group" means a $C_{1-6}$ alkoxy group or a $C_{1-6}$ alkoxy group having one or more substituents.

"$C_{1-6}$ alkoxy group" means a group represented by the formula: $C_{1-6}$ alkyl group-O—. The above description on "$C_{1-6}$ alkyl group" is also applied to a $C_{1-6}$ alkyl group contained in a $C_{1-6}$ alkoxy group.

In the $C_{1-6}$ alkoxy group having one or more substituents, one or more substituents each are substituted for a hydrogen atom of the $C_{1-6}$ alkoxy group. The number of substituents which may be possessed by the $C_{1-6}$ alkoxy group is preferably 1 to 3, and more preferably 1 or 2. When the number of substituents is 2 or more, two or more substituents may be the same or different from each other. One or more substituents which may be possessed by the $C_{1-6}$ alkoxy group each independently can be selected from a halogen atom.

Substituted or Unsubstituted $C_{2-6}$ Heteroalkyl Group

"Substituted or unsubstituted $C_{2-6}$ heteroalkyl group" means a $C_{2-6}$ heteroalkyl group or a $C_{2-6}$ heteroalkyl group having one or more substituents.

"$C_{2-6}$ heteroalkyl group" means a linear heteroalkyl group having 2 to 6 carbon atoms or a branched heteroalkyl group having 3 to 6 carbon atoms. "Heteroalkyl group" means an alkyl group having an oxygen atom (—O—) between carbon atoms. The number of oxygen atoms is preferably 1 or 2, and more preferably 1. The number of carbon atoms of the linear heteroalkyl group is preferably 2 to 5, more preferably 2 to 4, and still more preferably 2 or 3. The number of carbon atoms of the branched alkyl group is preferably 3 to 5, and more preferably 3 or 4. Examples of the $C_{2-6}$ heteroalkyl group include —$CH_2$—O—$CH_3$, —$CH_2$—$CH_2$—O—$CH_3$, —$CH_2$—$CH_2$—$CH_2$—O—$CH_3$, —CH(—$CH_3$)—$CH_2$—O—$CH_3$, —$CH_2$—O—$CH_2$—$CH_3$, —$CH_2$—$CH_2$—O—$CH_2$—$CH_3$, —$CH_2$—$CH_2$—$CH_2$—O—$CH_2$—$CH_3$, —CH(—$CH_3$)—$CH_2$—O—$CH_2$—$CH_3$, —$CH_2$—O—$CH_2$—$CH_2$—$CH_3$, —$CH_2$—$CH_2$—O—$CH_2$—$CH_2$—$CH_3$, —$CH_2$—$CH_2$—$CH_2$—O—$CH_2$—$CH_2$—$CH_3$, —CH(—$CH_3$)—$CH_2$—O—$CH_2$—$CH_2$—$CH_3$, —$CH_2$—O—CH(—$CH_3$)—$CH_3$, —$CH_2$—$CH_2$—O—CH(—$CH_3$)—$CH_3$, —$CH_2$—$CH_2$—$CH_2$—O—CH(—$CH_3$)—$CH_3$, —CH(—$CH_3$)—$CH_2$—O—CH(—$CH_3$)—$CH_3$ and the like.

In the $C_{2-6}$ heteroalkyl group having one or more substituents, one or more substituents each are substituted for a hydrogen atom of the $C_{2-6}$ heteroalkyl group. The number of substituents which may be possessed by the $C_{2-6}$ heteroalkyl group is preferably 1 to 3, and more preferably 1 or 2. When the number of substituents is 2 or more, two or more substituents may be the same or different from each other. One or more substituents which may be possessed by the $C_{2-6}$ heteroalkyl group each independently can be selected from a halogen atom.

Substituted or Unsubstituted $C_{7-6}$ Heteroalkoxy Group

"Substituted or unsubstituted $C_{2-6}$ heteroalkoxy group" means a $C_{2-6}$ heteroalkoxy group or a $C_{2-6}$ heteroalkoxy group having one or more substituents.

"$C_{2-6}$ heteroalkoxy group" means a group represented by the formula: $C_{2-6}$ heteroalkyl group-O—. The above description on "$C_{2-6}$ heteroalkyl group" is also applied to a $C_{2-6}$ heteroalkyl group contained in a $C_{2-6}$ heteroalkoxy group.

In the $C_{2-6}$ heteroalkoxy group having one or more substituents, one or more substituents each are substituted for a hydrogen atom of the $C_{2-6}$ heteroalkoxy group. The number of substituents which may be possessed by the $C_{2-6}$ heteroalkoxy group is preferably 1 to 3, and more preferably 1 or 2. When the number of substituents is 2 or more, two or more substituents may be the same or different from each other. One or more substituents which may be possessed by the $C_{2-6}$ heteroalkoxy group each independently can be selected from a halogen atom.

Substituted or Unsubstituted $C_{1-6}$ Monoalkylamino Group

"Substituted or unsubstituted $C_{1-6}$ monoalkylamino group" means a $C_{1-6}$ monoalkylamino group or a $C_{1-6}$ monoalkylamino group having one or more substituents.

"$C_{1-6}$ monoalkylamino group" is represented by the formula: —NH(-$Q^1$), wherein $Q^1$ is a $C_{1-6}$ alkyl group. The above description on "$C_{1-6}$ alkyl group" is also applied to a $C_{1-6}$ alkyl group contained in a $C_{1-6}$ monoalkylamino group.

In the $C_{1-6}$ monoalkylamino group having one or more substituents, one or more substituents each are substituted for a hydrogen atom of the $C_{1-6}$ monoalkylamino group. The number of substituents which may be possessed by the $C_{1-6}$ monoalkylamino group is preferably 1 to 3, and more preferably 1 or 2. When the number of substituents is 2 or more, two or more substituents may be the same or different from each other. One or more substituents which may be possessed by the $C_{1-6}$ monoalkylamino group each independently can be selected from a halogen atom.

Substituted or Unsubstituted $C_{7-6}$ Dialkylamino Group

"Substituted or unsubstituted $C_{2-6}$ dialkylamino group" means a $C_{2-6}$ dialkylamino group or a $C_{2-6}$ dialkylamino group having one or more substituents.

"$C_{2-6}$ dialkylamino group" is represented by the formula: —N(-$Q^2$)(-$Q^3$), wherein $Q^2$ and $Q^3$ each independently are a linear or branched $C_{1-3}$ alkyl group. The number of carbon atoms of the dialkylamino group is preferably 2 to 5, more preferably 2 to 4, and still more preferably 2 or 3. $Q^2$ and $Q^3$ each independently are preferably a linear $C_{1-3}$ alkyl group, and more preferably a methyl group or an ethyl group.

In the $C_{2-6}$ dialkylamino group having one or more substituents, one or more substituents each are substituted for a hydrogen atom of the $C_{2-6}$ dialkylamino group. The number of substituents which may be possessed by the $C_{2-6}$ dialkylamino group is preferably 1 to 3, and more preferably 1 or 2. When the number of substituents is 2 or more, two or more substituents may be the same or different from each other. One or more substituents which may be possessed by the $C_{2-6}$ dialkylamino group each independently can be selected from a halogen atom.

Substituted or Unsubstituted Alicyclic Group

"Substituted or unsubstituted alicyclic group" means an alicyclic group or an alicyclic group having one or more substituents.

"Alicyclic group" means a functional group produced by removing a hydrogen atom from a monocyclic aliphatic hydrocarbon ring. The alicyclic group is preferably a $C_{3-10}$ cycloalkyl group, more preferably a $C_{3-8}$ cycloalkyl group, and still more preferably a $C_{3-6}$ cycloalkyl group having. Examples of the $C_{3-10}$ cycloalkyl group include a cyclopropyl group, a cyclobutyl group, a cyclopentyl group, a cyclohexyl group, a cyclopentyl group, a cyclohexyl group, a cycloheptyl group, a cyclooctyl group and the like.

In the alicyclic group having one or more substituents, one or more substituents each are substituted for a hydrogen atom of the alicyclic group. The number of substituents which may be possessed by the alicyclic group is preferably 1 to 3, and more preferably 1 or 2. When the number of substituents is 2 or more, two or more substituents may be the same or different from each other. One or more substituents which may be possessed by the alicyclic group each independently can be selected from a halogen atom.

Substituted or Unsubstituted Alicyclic Oxy Group

"Substituted or unsubstituted alicyclic oxy group" means an alicyclic oxy group or an alicyclic oxy group having one or more substituents.

"Alicyclic oxy group" means a group represented by the formula: alicyclic group-O—. The above description on "alicyclic group" is also applied to an alicyclic group contained in an alicyclic oxy group.

In the alicyclic oxy group having one or more substituents, one or more substituents each are substituted for a hydrogen atom of the alicyclic oxy group. The number of substituents which may be possessed by the alicyclic oxy group is preferably 1 to 3, and more preferably 1 or 2. When the number of substituents is 2 or more, two or more substituents may be the same or different from each other.

One or more substituents which may be possessed by the alicyclic oxy group each independently can be selected from a halogen atom.

Substituted or Unsubstituted Aliphatic Heterocyclic Group

"Substituted or unsubstituted aliphatic heterocyclic group" means an aliphatic heterocyclic group or an aliphatic heterocyclic group having one or more substituents.

"Aliphatic heterocyclic group" means a functional group produced by removing a hydrogen atom from a monocyclic aliphatic heterocycle (non-aromatic heterocycle) containing one or more heteroatoms independently selected from the group consisting of an oxygen atom, a sulfur atom and a nitrogen atom in addition to a carbon atom, as a ring-constituting atom.

The number of heteroatoms contained in the aliphatic heterocyclic group is usually 1 to 4, preferably 1 to 3, and more preferably 1 or 2. The number of members of the aliphatic heterocyclic group is usually 3 to 8, preferably 4 to 8, more preferably 5 to 7, and still more preferably 5 or 6. The number of ring-constituting carbon atoms in the aliphatic heterocyclic group is appropriately determined according to the number of heteroatoms and the number of members of the aliphatic heterocyclic group.

The aliphatic heterocyclic group is, for example, a saturated aliphatic heterocyclic group. The saturated aliphatic heterocyclic group is an aliphatic heterocyclic group in which a ring is constituted only by a saturated bond. Examples of the saturated aliphatic heterocyclic group include a group containing 1 to 2 oxygen atoms, a group containing 1 to 2 sulfur atoms, a group containing 1 to 2 oxygen atoms and 1 to 2 sulfur atoms, a group containing 1 to 4 nitrogen atoms, a group containing 1 to 3 nitrogen atoms and 1 to 2 sulfur atoms and/or 1 to 2 oxygen atoms and the like. In the saturated aliphatic heterocyclic group, two carbon atoms constituting the ring may be cross-linked by an alkylene group. In the saturated aliphatic heterocyclic group, two adjacent carbon atoms among ring-constituting carbon atoms may form a double bond. In the saturated aliphatic heterocyclic group, two hydrogen atoms bonded to the same carbon atom may be substituted with an oxo group. The number of oxo groups which may be possessed by the saturated aliphatic heterocyclic group is preferably 1 or 2. When the saturated aliphatic heterocyclic group contains a sulfur atom, the saturated aliphatic heterocyclic group may be a dioxide form.

Examples of the aliphatic heterocyclic group include 3- to 8-membered aliphatic heterocyclic groups such as an aziridinyl group, an oxiranyl group, a thiiranyl group, an azetidinyl group, an oxetanyl group, a thiethanyl group, a tetrahydrothienyl group, a tetrahydrofuranyl group, a pyrrolinyl group, a pyrrolidinyl group, an imidazolinyl group, an imidazolidinyl group, an oxazolinyl group, an oxazolidinyl group, a pyrazolinyl group, a pyrazolidinyl group, a thiazolinyl group, a thiazolidinyl group, a tetrahydroisothiazolyl group, a tetrahydrooxazolyl group, a tetrahydroisooxazolyl group, a piperidinyl group, a piperazinyl group, a tetrahydropyridinyl group, a dihydropyridinyl group, a dihydrothiopyranyl group, a tetrahydropyrimidinyl group, a tetrahydropyridazinyl group, a dihydropyranyl group, a tetrahydropyranyl group, a tetrahydrothiopyranyl group, a morpholinyl group, a thiomorpholinyl group (a sulfur atom on the ring may be oxidized), an azepanyl group, a diazepanyl group, an azepinyl group, an oxepanyl group, an azocanyl group and a diazocanyl group.

The aliphatic heterocyclic group is preferably a tetrahydrofuranyl group.

In the aliphatic heterocyclic group having one or more substituents, one or more substituents each are substituted for a hydrogen atom of the aliphatic heterocyclic group. The number of substituents which may be possessed by the aliphatic heterocyclic group is preferably 1 to 3, and more preferably 1 or 2. When the number of substituents is 2 or more, two or more substituents may be the same or different from each other. One or more substituents which may be possessed by the aliphatic heterocyclic group each independently can be selected from a halogen atom.

Substituted or Unsubstituted Aliphatic Heterocyclic Oxy Group

"Substituted or unsubstituted aliphatic heterocyclic oxy group" means an aliphatic heterocyclic oxy group or an aliphatic heterocyclic oxy group having one or more substituents.

"Aliphatic heterocyclic oxy group" means a group represented by the formula: aliphatic heterocyclic group-O—. The above description on "aliphatic heterocyclic group" is also applied to an aliphatic heterocyclic group contained in an aliphatic heterocyclic oxy group.

The aliphatic heterocyclic oxy group is preferably a tetrahydrofuranyl oxy group.

In the aliphatic heterocyclic oxy group having one or more substituents, one or more substituents each are substituted for a hydrogen atom of the aliphatic heterocyclic oxy group. The number of substituents which may be possessed by the aliphatic heterocyclic oxy group is preferably 1 to 3, and more preferably 1 or 2. When the number of substituents is 2 or more, two or more substituents may be the same or different from each other. One or more substituents which may be possessed by the aliphatic heterocyclic oxy group each independently can be selected from a halogen atom.

Substituted or Unsubstituted Phenyl Group

"Substituted or unsubstituted phenyl group" means a phenyl group or a phenyl group having one or more substituents.

In the phenyl group having one or more substituents, one or more substituents each are substituted for a hydrogen atom of the phenyl group. The number of substituents which may be possessed by the phenyl group is preferably 1 to 4, more preferably 1 to 3, and still more preferably 1 or 2. When the number of substituents is 2 or more, two or more substituents may be the same or different from each other. One or more substituents which may be possessed by the phenyl group each independently can be selected from the substituent group α mentioned below. When one or more substituents are selected from a group containing a carbon atom, the total number of carbon atoms in the phenyl group having one or more substituents is preferably 10 or less, more preferably 9 or less, still more preferably 8 or less, and yet more preferably 7 or less.

Substituted or Unsubstituted Phenyloxy Group

"Substituted or unsubstituted phenyloxy group" means a phenyloxy group or a phenyloxy group having one or more substituents.

"Phenyloxy group" means a group represented by the formula: phenyl group-O—.

In the phenyloxy group having one or more substituents, one or more substituents each are substituted for a hydrogen atom of the phenyloxy group. The number of substituents which may be possessed by the phenyloxy group is preferably 1 to 4, more preferably 1 to 3, and still more preferably 1 or 2. When the number of substituents is 2 or more, two or more substituents may be the same or different from each other. One or more substituents which may be possessed by the phenyloxy group each independently can be selected from the substituent group α mentioned below. When one or more substituents are selected from a group containing a carbon atom, the total number of carbon atoms in the phenyloxy group having one or more substituents is preferably 12 or less, more preferably 10 or less, and still more preferably 8 or less.

Substituted or Unsubstituted $C_{7-10}$ Phenylalkyl Group

"Substituted or unsubstituted $C_{7-10}$ phenylalkyl group" means a $C_{7-10}$ phenylalkyl group or a $C_{7-10}$ phenylalkyl group having one or more substituents.

"$C_{7-10}$ phenylalkyl group" means a group represented by the formula: phenyl group-$C_{1-4}$ alkylene group. "$C_{1-4}$ alkylene group" means a linear alkylene group having 1 to 4 carbon atoms or a branched alkylene group having 3 to 4 carbon atoms. The $C_{1-4}$ alkylene group is preferably a linear $C_{1-4}$ alkylene group. The number of carbon atoms of the linear alkylene group is preferably 1 to 3, and more preferably 1 or 2.

In the $C_{7-10}$ phenylalkyl group having one or more substituents, one or more substituents each are substituted for a hydrogen atom of the phenylalkyl group. The hydrogen atom to be substituted may be a hydrogen atom on the benzene ring or may be a hydrogen atom of the alkylene part, but is preferably a hydrogen atom on the benzene ring. The number of substituents which may be possessed by the phenylalkyl group in the alkylene part is preferably 1 to 3, and more preferably 1 or 2, and the number of substituents which may be possessed by the phenylalkyl group on the benzene ring is preferably 1 to 4, more preferably 1 to 3, and still more preferably 1 or 2. When the number of substituents is 2 or more, two or more substituents may be the same or different from each other. One or more substituents which may be possessed by the phenylalkyl group each independently can be selected from the substituent group α mentioned below. When one or more substituents are selected from a group containing a carbon atom, the total number of carbon atoms in the phenylalkyl group having one or more substituents is preferably 16 or less, more preferably 14 or less, and still more preferably 12 or less.

Substituted or Unsubstituted $C_{7-10}$ Phenylalkyloxy Group

"Substituted or unsubstituted $C_{7-10}$ phenylalkyloxy group" means a $C_{7-10}$ phenylalkyloxy group or a $C_{7-10}$ phenylalkyloxy group having one or more substituents.

"$C_{7-10}$ phenylalkyloxy group" means a group represented by the formula: $C_{7-10}$ phenylalkyl group-O—. The above description on "$C_{7-10}$ phenylalkyl group" is also applied to a $C_{7-10}$ phenylalkyl group contained in a $C_{7-10}$ phenylalkyloxy group.

In the $C_{7-10}$ phenylalkyloxy group having one or more substituents, one or more substituents each are substituted for a hydrogen atom of the phenylalkyloxy group. The hydrogen atom to be substituted may be a hydrogen atom on the benzene ring or may be a hydrogen atom of the alkylene part, but is preferably a hydrogen atom on the benzene ring. The number of substituents which may be possessed by the phenylalkyloxy group in the alkylene part is preferably 1 to 3, and more preferably 1 or 2, and the number of substituents which may be possessed by the phenylalkyloxy group on the benzene ring is preferably 1 to 4, more preferably 1 to 3, and still more preferably 1 or 2. When the number of substituents is 2 or more, two or more substituents may be the same or different from each other. One or more substituents which may be possessed by the phenylalkyloxy group each independently can be selected from the substituent group α mentioned below. When one or more substituents are selected from a group containing a carbon atom, the total number of carbon atoms in the phenylalkyloxy group having one or more substituents is preferably 16 or less, more preferably 14 or less, and still more preferably 12 or less.

Substituent Group α

"Substituent group α" is composed of the following substituents.

(α-1) Halogen atom
(α-2) Amino group
(α-3) Substituted or unsubstituted $C_{1-6}$ alkyl group
(α-4) Substituted or unsubstituted $C_{1-6}$ alkoxy group
(α-5) Substituted or unsubstituted $C_{2-6}$ heteroalkyl group
(α-6) Substituted or unsubstituted $C_{2-6}$ heteroalkoxy group
(α-7) Substituted or unsubstituted $C_{1-6}$ monoalkylamino group
(α-8) Substituted or unsubstituted $C_{2-6}$ dialkylamino group
(α-9) Substituted or unsubstituted alicyclic group
(α-10) Substituted or unsubstituted alicyclic oxy group
(α-11) Substituted or unsubstituted aliphatic heterocyclic group
(α-12) Substituted or unsubstituted aliphatic heterocyclic oxy group The above descriptions on "halogen atom", "substituted or unsubstituted $C_{1-6}$ alkyl group", "substituted or unsubstituted $C_{1-6}$ alkoxy group", "substituted or unsubstituted $C_{2-6}$ heteroalkyl group", "substituted or unsubstituted $C_{2-6}$ heteroalkoxy group", "substituted or unsubstituted $C_{1-6}$ monoalkylamino group", "substituted or unsubstituted $C_{2-6}$ dialkylamino group", "substituted or unsubstituted alicyclic group", "substituted or unsubstituted alicyclic oxy group", "substituted or unsubstituted aliphatic heterocyclic group" and "substituted or unsubstituted aliphatic heterocyclic oxy group" are also applied to the substituent group α.

The substituent group α is preferably composed of a halogen atom, a substituted or unsubstituted $C_{1-6}$ alkyl group, a substituted or unsubstituted $C_{1-6}$ alkoxy group, a substituted or unsubstituted $C_{2-6}$ heteroalkyl group, a substituted or unsubstituted $C_{2-6}$ heteroalkoxy group, a substituted or unsubstituted aliphatic heterocyclic group and a substituted or unsubstituted aliphatic heterocyclic oxy group, more preferably composed of a halogen atom, a substituted or unsubstituted $C_{1-6}$ alkyl group, a substituted or unsubstituted $C_{1-6}$ alkoxy group, a substituted or unsubstituted $C_{2-6}$ heteroalkyl group and a substituted or unsubstituted $C_{2-6}$ heteroalkoxy group, and still more preferably composed of a halogen atom, a substituted or unsubstituted $C_{1-6}$ alkyl group and a substituted or unsubstituted $C_{1-6}$ alkoxy group.

Substituted or Unsubstituted Aromatic Ring Group

"Substituted or unsubstituted aromatic ring group" means an aromatic ring group or an aromatic ring group having one or more substituents.

"Aromatic ring group" means a group produced by removing a hydrogen atom from a monocyclic or fused polycyclic aromatic hydrocarbon ring. The aromatic ring group is usually a 1- to 4-cyclic, preferably 1- to 3-cyclic, and more preferably 1- or 2-cyclic aromatic ring group. The number of ring-constituting carbon atoms in the aromatic ring group is usually 6 to 18, preferably 6 to 14, and more preferably 6 to 10. Examples of the monocyclic aromatic ring group include a phenyl group. Examples of the fused polycyclic aromatic ring group include 2- to 4-cyclic aromatic ring groups, such as a naphthyl group, an anthryl group, a phenanthrenyl group, a tetracenyl group and a pyrenyl group, and the like. The fused polycyclic aromatic ring group may be a fused polycyclic aromatic ring group which was partially saturated. The fused polycyclic aromatic ring group which was partially saturated is a fused polycyclic aromatic ring group in which a part of bonds constituting the ring was hydrogenated.

The aromatic ring group is preferably a phenyl group.

In the aromatic ring group having one or more substituents, one or more substituents each are substituted for a hydrogen atom of the aromatic ring group. The number of substituents which may be possessed by the aromatic ring group can be appropriately determined according to the number of carbon atoms and the number of members of the aromatic ring group. The number of substituents which may be possessed by the aromatic ring group is preferably 1 to 4, more preferably 1 to 3, and still more preferably 1 or 2. When the number of substituents is 2 or more, two or more substituents may be the same or different from each other. One or more substituents which may be possessed by the aromatic ring group each independently can be selected from the substituent group β mentioned below. When one or more substituents are selected from a group containing a carbon atom, the total number of carbon atoms in the aromatic ring group having one or more substituents is preferably 20 or less, more preferably 19 or less, still more preferably 18 or less, and yet more preferably 17 or less.

Substituted or Unsubstituted Aromatic Heterocyclic Group

"Substituted or unsubstituted aromatic heterocyclic group" means an aromatic heterocyclic group or an aromatic heterocyclic group having one or more substituents.

"Aromatic heterocyclic group" means a group produced by removing a hydrogen atom from a monocyclic or fused polycyclic aromatic heterocycle containing one or more heteroatoms independently selected from the group consisting of an oxygen atom, a sulfur atom and a nitrogen atom in addition to a carbon atom, as a ring-constituting atom. The aromatic heterocyclic group is usually a 1- to 4-cyclic, preferably 1- to 3-cyclic, and more preferably 1- or 2-cyclic aromatic heterocyclic group. The number of heteroatoms contained in the aromatic heterocyclic group is usually 1 to 4, preferably 1 to 3, and still more preferably 1 or 2. The number of members of the aromatic heterocyclic group is preferably 5 to 14, and more preferably 5 to 10. The number of ring-constituting carbon atoms in the aromatic heterocyclic group is appropriately determined according to the number of heteroatoms and the number of members of the aromatic heterocyclic group. In the aromatic heterocyclic group, two hydrogen atoms bonded to the same carbon atom may be substituted with an oxo group.

The aromatic heterocyclic group is, for example, a monocyclic aromatic heterocyclic group. The monocyclic aromatic heterocyclic group is, for example, a 5- to 7-membered monocyclic aromatic heterocyclic group. Examples of the monocyclic aromatic heterocyclic group include a group containing 1 to 2 oxygen atoms, a group containing 1 to 2 sulfur atoms, a group containing 1 to 2 oxygen atoms and 1 to 2 sulfur atoms, a group containing 1 to 4 nitrogen atoms, a group containing 1 to 3 nitrogen atoms and 1 to 2 sulfur atoms and/or 1 to 2 oxygen atoms and the like.

Examples of the monocyclic aromatic heterocyclic group include 5- to 7-membered monocyclic aromatic heterocyclic groups such as a pyridyl group, a pyridazinyl group, a pyrimidinyl group, a pyrazinyl group, a thienyl group, a pyrrolyl group, a thiazolyl group, an isothiazolyl group, a pyrazolyl group, an imidazolyl group, a furyl group, an oxazolyl group, an isoxazolyl group, an oxadiazolyl group (e.g., a 1,2,4-oxadiazolyl group, a 1,3,4-oxadiazolyl group, etc.), a thiadiazolyl group (e.g., a 1,2,4-thiadiazolyl group, a 1,3,4-thiadiazolyl group, etc.), a triazolyl group (e.g., a 1,2,3-triazolyl group, a 1,2,4-triazolyl group, etc.), a tetrazolyl group and a triazinyl group. In the monocyclic aromatic heterocyclic group, two hydrogen atoms bonded to the same carbon atom may be substituted with an oxo group. The number of oxo groups which may be possessed by the monocyclic aromatic heterocyclic group is preferably 1 or 2.

The aromatic heterocyclic group is, for example, a fused polycyclic aromatic heterocyclic group. The fused polycyclic aromatic heterocyclic group is, for example, an 8- to 14-membered 2-cyclic or 3-cyclic aromatic heterocyclic group. Examples of the fused polycyclic aromatic heterocyclic group include a group containing 1 to 3 oxygen atoms, a group containing 1 to 3 sulfur atoms, a group containing 1 to 3 oxygen atoms and 1 to 3 sulfur atoms, a group containing 1 to 5 nitrogen atoms, a group containing 1 to 4 nitrogen atoms and 1 to 3 sulfur atoms and/or 1 to 3 oxygen atoms and the like.

Examples of the fused polycyclic aromatic heterocyclic group include 8- to 14-membered fused polycyclic (preferably 2-cyclic or 3-cyclic) aromatic heterocyclic groups, such as a benzothiophenyl group, a benzofuranyl group, a benzoimidazolyl group, a benzooxazolyl group, a benzoisoxazolyl group, a benzothiazolyl group, a benzoisothiazolyl group, a benzotriazolyl group, an imidazopyridinyl group, a thienopyridinyl group, a furopyridinyl group, a pyrrolopyridinyl group, a pyrazolopyridinyl group, an oxazolopyridinyl group, a thiazolopyridinyl group, an imidazopyrazinyl group, an imidazopyrimidinyl group, a thienopyrimidinyl group, a furopyrimidinyl group, a pyrrolopyrimidinyl group, a pyrazolopyrimidinyl group, an oxazolopyrimidinyl group, a thiazolopyrimidinyl group, a pyrazolotriazinyl group, a naphtho[2,3-b]thienyl group, a phenoxathiinyl group, an indolyl group, an isoindolyl group, a 1H-indazolyl group, a purinyl group, an isoquinolyl group, a quinolyl group, a phthalazinyl group, a naphthyridinyl group, a quinoxalinyl group, a quinazolinyl group, a cinnolinyl group, a carbazolyl group, an α-carbolinyl group, a phenanthridinyl group, an acridinyl group, a phenazinyl group, a phenothiazinyl group and a phenoxazinyl group, and the like. In the polycyclic aromatic heterocyclic group, two hydrogen atoms bonded to the same carbon atom may be substituted with an oxo group. The number of oxo groups which may be possessed by the polycyclic aromatic heterocyclic group is preferably 1, 2 or 3.

The aromatic heterocyclic group is preferably a thienyl group, a benzothiophenyl group, a furyl group, a pyrrolyl group, an imidazolyl group or a pyridyl group, and still more preferably a thienyl group or a benzothiophenyl group.

In the aromatic heterocyclic group having one or more substituents, one or more substituents each are substituted for a hydrogen atom of the aromatic heterocyclic group. The number of substituents which may be possessed by the aromatic heterocyclic group can be appropriately determined according to the number of carbon atoms and the number of members of the aromatic heterocyclic group. The number of substituents which may be possessed by the aromatic heterocyclic group is preferably 1 to 4, more preferably 1 to 3, and still more preferably 1 or 2. When the number of substituents is 2 or more, two or more substituents may be the same or different from each other. One or more substituents which may be possessed by the aromatic heterocyclic group each independently can be selected from the substituent group β mentioned below. When one or more substituents are selected from a group containing a carbon atom, the total number of carbon atoms in the aromatic heterocyclic group having one or more substituents is preferably 20 or less, more preferably 19 or less, still more preferably 18 or less, and yet more preferably 17 or less.

Substituent Group β "Substituent group β" is composed of the following substituents.

(β-1) Substituent group a
(β-2) Substituted or unsubstituted phenyl group
(β-3) Substituted or unsubstituted phenyloxy group
(β-4) Substituted or unsubstituted $C_{7-10}$ phenylalkyl group
(β-5) Substituted or unsubstituted $C_{7-10}$ phenylalkyloxy group The above descriptions on "substituent group α", "substituted or unsubstituted phenyl group", "substituted or unsubstituted phenyloxy group", "substituted or unsubstituted $C_{7-10}$ phenylalkyl group" and "substituted or unsubstituted $C_{7-10}$ phenylalkyloxy group" are also applied to the substituent group β.

(β-2) is preferably a phenyl group having one or more substituents selected from a halogen atom. The number of halogen atom(s) is preferably 1 to 4, more preferably 1 to 3, and still more preferably 1 or 2.

(β-3) is preferably a phenyloxy group having one or more substituents selected from a halogen atom. The number of halogen atom(s) is preferably 1 to 4, more preferably 1 to 3, and still more preferably 1 or 2.

(β-4) is preferably a $C_{7-10}$ phenylalkyl group having one or more substituents selected from a halogen atom. The number of halogen atom(s) is preferably 1 to 4, more preferably 1 to 3, and still more preferably 1 or 2.

(β-5) is preferably a $C_{7-10}$ phenylalkyloxy group having one or more substituents selected from a halogen atom. The number of halogen atom(s) is preferably 1 to 4, more preferably 1 to 3, and still more preferably 1 or 2.

The substituent group β is preferably composed of a halogen atom, an aliphatic heterocyclic oxy group, a phenyl group, and a phenyl group having one or more substituents selected from a halogen atom and an aliphatic heterocyclic oxy group, and more preferably composed of a halogen atom, an aliphatic heterocyclic oxy group, a phenyl group, and a phenyl group having one or more substituents selected from a halogen atom.

Compound (1)

A compound (1) is a compound represented by the following formula (1):

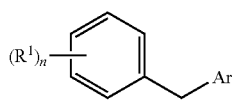
(1)

In formula (1), n is an integer of 0 to 5. n is preferably 2 or 3. When n is 2 or 3, the compound (1) is particularly useful as a synthetic intermediate for an active pharmaceutical ingredient of an antidiabetic drug or the like.

In formula (1), $(R^1)_n$ each independently are a group selected from a halogen atom, an amino group, a substituted or unsubstituted $C_{1-6}$ alkyl group, a substituted or unsubstituted $C_{1-6}$ alkoxy group, a substituted or unsubstituted $C_{2-6}$ heteroalkyl group, a substituted or unsubstituted $C_{2-6}$ heteroalkoxy group, a substituted or unsubstituted $C_{1-6}$ monoalkylamino group, a substituted or unsubstituted $C_{2-6}$ dialkylamino group, a substituted or unsubstituted alicyclic group, a substituted or unsubstituted alicyclic oxy group, a substituted or unsubstituted aliphatic heterocyclic group, a substituted or unsubstituted aliphatic heterocyclic oxy group, a substituted or unsubstituted phenyl group, a substituted or unsubstituted phenyloxy group, a substituted or unsubstituted $C_{7-10}$ phenylalkyl group and a substituted or unsubstituted $C_{7-10}$ phenylalkyloxy group. When n is 2 or more, $(R^L)_n$ may be the same or different from each other.

In formula (1), $(R^L)_n$ each independently are preferably a group selected from a halogen atom, a substituted or unsubstituted $C_{1-6}$ alkyl group, a substituted or unsubstituted $C_{1-6}$ alkoxy group, a substituted or unsubstituted $C_{2-6}$ heteroalkyl group, a substituted or unsubstituted $C_{2-6}$ heteroalkoxy group, a substituted or unsubstituted alicyclic group, a substituted or unsubstituted alicyclic oxy group, a substituted or unsubstituted aliphatic heterocyclic group, a substituted or unsubstituted aliphatic heterocyclic oxy group, a substituted or unsubstituted phenyl group, a substituted or unsubstituted phenyloxy group, a substituted or unsubstituted $C_{7-10}$ phenylalkyl group and a substituted or unsubstituted $C_{7-10}$ phenylalkyloxy group, more preferably a group selected from a halogen atom, a substituted or unsubstituted $C_{1-6}$ alkyl group, a substituted or unsubstituted $C_{1-6}$ alkoxy group, a substituted or unsubstituted phenyl group and a substituted or unsubstituted $C_{7-10}$ phenylalkyl group, still more preferably a group selected from fluorine, bromine, iodine, a methyl group, an ethyl group, an isopropyl group, a tert-butyl group, a methoxy group, an ethoxy group, a phenyl group and a benzyl group, and yet more preferably a group selected from fluorine, bromine, iodine, a methyl group and a methoxy group. When $(R^1)_n$ each independently are selected from these groups, the compound (1) is particularly useful as a synthetic intermediate for an active pharmaceutical Ingredient of an antidiabetic drug or the like.

In formula (1), when n is 2, the positions at which two $R^1$ are bonded are preferably positions 2 and 5 of the benzene ring. Position 1 is a position at which —$CH_2$—Ar is bonded.

In formula (1), when n is 2, at least one of two $R^1$ is preferably a halogen atom. When the positions of two $R^1$ are positions 2 and 5 of the benzene ring, at least $R^1$ at position 5 is preferably a halogen atom. The combination of two $R^1$ is preferably a combination of a halogen atom and one selected from a halogen atom, a substituted or unsubstituted $C_{1-6}$ alkyl group and a substituted or unsubstituted $C_{1-6}$ alkoxy group, and more preferably a combination of a halogen atom and one selected from a halogen atom and a substituted or unsubstituted $C_{1-6}$ alkyl group.

In formula (1), when n is 3, the positions at which three $R^1$ are bonded are preferably positions 2, 4 and 5 of the benzene ring. Position 1 is a position at which —$CH_2$—Ar is bonded.

In formula (1), when n is 3, at least one of three $R^1$ is preferably a halogen atom. When the positions of three $R^1$ are positions 2, 4 and 5 of the benzene ring, at least $R^1$ at position 5 is preferably a halogen atom. The combination of three $R^1$ is preferably a combination of a halogen atom and two selected from a halogen atom, a substituted or unsubstituted $C_{1-6}$ alkyl group and a substituted or unsubstituted $C_{1-6}$ alkoxy group, more preferably a combination of a halogen atom, a halogen atom and one selected from a substituted or unsubstituted $C_{1-6}$ alkyl group and a substituted or unsubstituted $C_{1-6}$ alkoxy group or a combination of a halogen atom and two selected from a substituted or unsubstituted $C_{1-6}$ alkyl group and a substituted or unsubstituted $C_{1-6}$ alkoxy group, and still more preferably a combination of a halogen atom, a substituted or unsubstituted $C_{1-6}$ alkyl group and a substituted or unsubstituted $C_{1-6}$ alkoxy group.

In formula (1), Ar is a group selected from a substituted or unsubstituted aromatic ring group and a substituted or unsubstituted aromatic heterocyclic group.

In formula (1), Ar is preferably a group represented by the following formula (Ar-1), (Ar-2) or (Ar-3).

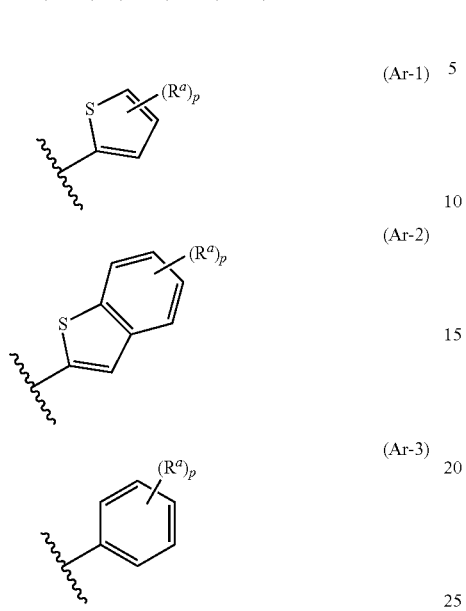

In formulas (Ar-1), (Ar-2) and (Ar-3), p is an integer of 0 to 5. p is preferably an integer of 0 to 3, more preferably an integer of 0 to 2, and still more preferably 0 or 1.

In formulas (Ar-1), (Ar-2) and (Ar-3), $(R^a)_p$ each independently are a group selected from a halogen atom, an amino group, a substituted or unsubstituted $C_{1-6}$ alkyl group, a substituted or unsubstituted $C_{1-6}$ alkoxy group, a substituted or unsubstituted $C_{2-6}$ heteroalkyl group, a substituted or unsubstituted $C_{2-6}$ heteroalkoxy group, a substituted or unsubstituted $C_{1-6}$ monoalkylamino group, a substituted or unsubstituted $C_{2-6}$ dialkylamino group, a substituted or unsubstituted alicyclic group, a substituted or unsubstituted alicyclic oxy group, a substituted or unsubstituted aliphatic heterocyclic group, a substituted or unsubstituted aliphatic heterocyclic oxy group, a substituted or unsubstituted phenyl group, a substituted or unsubstituted phenyloxy group, a substituted or unsubstituted $C_{7-10}$ phenylalkyl group and a substituted or unsubstituted $C_{7-10}$ phenylalkyloxy group.

In formula (Ar-1), p is preferably 1, and $R^a$ is preferably a substituted or unsubstituted phenyl group, more preferably a phenyl group having a halogen atom, and still more preferably a phenyl group having a fluorine atom. The position at which the substituted or unsubstituted phenyl group is bonded is preferably position 2 of the thiophene ring. In the phenyl group having a halogen atom, the position at which the halogen atom is bonded is preferably position 4 of the benzene ring.

In formula (Ar-2), p is preferably 0.

In formula (Ar-3), p is preferably 1, and $R^a$ is preferably a substituted or unsubstituted $C_{1-6}$ alkoxy group, more preferably a $C_{1-3}$ alkoxy group, and still more preferably a methoxy group or an ethoxy group. The position at which the substituted or unsubstituted $C_{1-6}$ alkoxy group is bonded is preferably position 4 of the benzene ring.

Examples of suitable compounds among the compounds (1) represented by formula (1) include the following compounds.

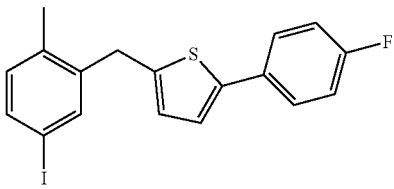

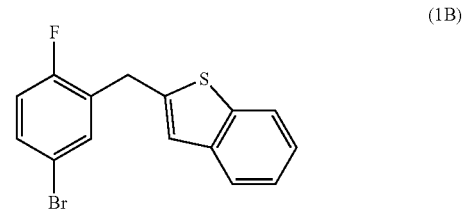

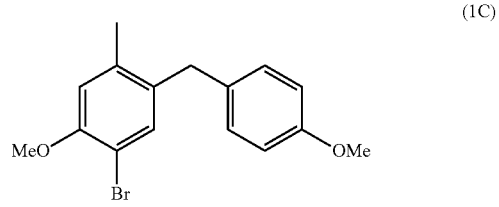

A compound (1A) is useful as a synthetic intermediate for canagliflozin, a compound (1B) is useful as a synthetic intermediate for ipragliflozin, and a compound (1C) is useful as a synthetic intermediate for luseogliflozin. All of canagliflozin, ipragliflozin and luseogliflozin are antidiabetic drugs.

Compound (2)

A compound (2) is a compound represented by the following formula (2):

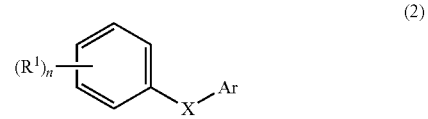

In formula (2), $R^1$, Ar and n are the same as in formula (1). Therefore, the above descriptions on $R^1$, Ar and n in formula (1) are also applied to $R^1$, Ar and n in formula (2).

In formula (2), X is a group selected from —C(=O)—, —CH(—OH)— and —CH(—OR²)—.

$R^2$ is a group selected from a substituted or unsubstituted $C_{1-6}$ alkyl group and a substituted or unsubstituted $C_{7-10}$ phenylalkyl group. $R^2$ is preferably a group selected from a $C_{1-6}$ alkyl group and a $C_{7-10}$ phenylalkyl group, more preferably a group selected from a $C_{1-3}$ alkyl group and a $C_{7-10}$ phenylalkyl group, and still more preferably a group selected from a methyl group, an ethyl group and a benzyl group.

When X is —C(=O)—, the compound (2) is a ketone compound (2-1) represented by the following formula (2-1):

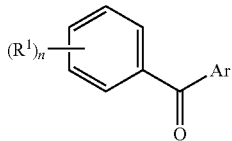
(2-1)

wherein $R^1$, Ar and n are the same as defined above.

When X is —CH(—OH)—, the compound (2) is an alcohol compound (2-2) represented by the following formula (2-2):

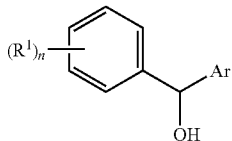
(2-2)

wherein $R^1$, Ar and n are the same as defined above.

When X is —CH(—OR$^2$)—, the compound (2) is an ether compound (2-3) represented by the following formula (2-3):

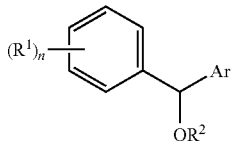
(2-3)

wherein $R^1$, Ar, n and $R^2$ are the same as defined above.

In formula (2), X is preferably —C(=O)— or —CH(—OH)—. In other words, the compound (2) is preferably a ketone compound (2-1) or an alcohol compound (2-2). The ketone compound (2-1) and the alcohol compound (2-2) are particularly useful as a synthetic intermediate for an active pharmaceutical ingredient of an antidiabetic drug or the like.

Examples of suitable compounds among the ketone compounds (2-1) include the following compounds.

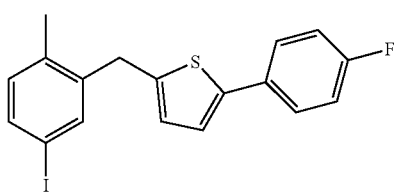
(2-1A)

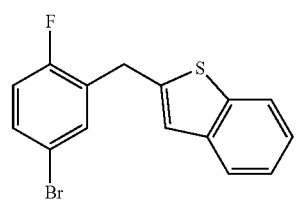
(2-1B)

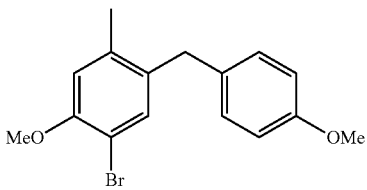
(2-1C)

Examples of suitable compounds among the alcohol compounds (2-2) include compounds derived from the ketone compounds (2-1A) to (2-1C) by replacing =O by —OH. The compounds derived from the ketone compounds (2-1A) to (2-1C) by replacing =O by —OH are referred to as alcohol compounds (2-2A) to (2-2C), respectively. An alcohol compound (2-2B) derived from the ketone compound (2-1B) by replacing =O by —OH is shown below.

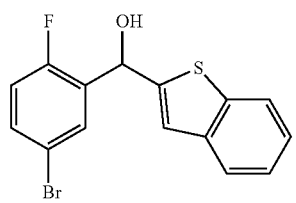
(2-2B)

The ketone compound (2-1A) and the alcohol compound (2-2A) are useful as a synthetic intermediate for canagliflozin, the ketone compound (2-1B) and the alcohol compound (2-2B) are useful as a synthetic intermediate for ipragliflozin, and the ketone compound (2-1C) and the alcohol compound (2-2C) are useful as a synthetic intermediate for luseogliflozin. All of canagliflozin, ipragliflozin and luseogliflozin are antidiabetic drugs.

Titanium Compound

As a titanium compound, for example, there have been known a compound in which titanium is zerovalent, a compound in which titanium is divalent, a compound in which titanium is trivalent, a compound in which titanium is tetravalent and the like, but any of these titanium compound may be used. Examples of the titanium compound include a tetravalent titanium salt, such as $TiCl_4$, $TiBr_4$, $TiI_4$, $TiO_2$, $Ti(O\text{-}iPr)Cl_3$, $Ti(O\text{-}iPr)_2Cl_2$ and $Ti(O\text{-}iPr)_3Cl$, or a solvate thereof; a trivalent titanium salt, such as $TiCl_3$, $TiBr_3$ and $TiO_3$, or a solvate thereof; a divalent titanium salt, such as $TiCl_2$ and TiO, or a solvate thereof; and zerovalent titanium, such as metal Ti, or a solvate thereof. "iPr" means an isopropyl group. Examples of the solvate include a hydrate and the like.

In terms of reactivity and easy handling in the reaction system, the titanium compound is preferably a trivalent or tetravalent titanium salt represented by the following formula (3):

$$TiR^3{}_r(OR^4)_s \qquad (3)$$

wherein $R^3$ is a halogen atom, $R^4$ is a substituted or unsubstituted $C_{1\text{-}6}$ alkyl group, and r and s are integers of 0 to 4 satisfying r+s=3 or 4, or a solvate thereof, and more preferably a titanium tetrachloride or a solvate thereof.

In formula (3), $R^3$ is preferably a chlorine atom, a bromine atom or an iodine atom, and $R^4$ is preferably a $C_{1\text{-}3}$ alkyl group. The above description on "substituted or unsubstituted $C_{1-6}$ alkyl group" is also applied to $R^4$ in formula (3).

<First Aspect>

The first aspect of the present invention relates to a method for producing a compound (1), which includes the following steps (a) and (b):

(a) a step of providing a compound (2); and
(b) a step of reducing the compound (2) in the presence of a titanium compound by using a reducing agent to produce the compound (1).

Step (a)

The compound (2) to be provided in the step (a) may be an industrially and commercially available product, or may be a compound produced in the step (a).

The step (a) can include a step of producing the compound (2). In the step of producing the compound (2), it is possible to produce the compound (2) by using a production method according to the third aspect of the present invention. When the step (a) includes a step of producing a ketone compound (2-1), it is possible to produce a ketone compound (2-1) by using a production method according to Aspect 3A. When the step (a) includes a step of producing an alcohol compound (2-2), it is possible to produce an alcohol compound (2-2) by using a production method according to Aspect 3B. When the step (a) includes a step of producing an ether compound (2-3), it is possible to produce an ether compound (2-3) by using a production method according to Aspect 3C.

Step (b)

In the step (b), the compound (2) is reduced in the presence of a titanium compound by using a reducing agent to produce the compound (1). In the step (b), the titanium compound acts as a Lewis acid. By using the titanium compound, it is possible to efficiency produce the compound (1) in a high yield.

The description on "titanium compound" herein is also applied to the titanium compound used in the step (b).

Examples of the reducing agent used in the step (b) include a reducing agent which is used in a reduction reaction and has a carbonyl group, an ether group, an alkoxide group and the like. Specific examples of the reducing agent include silane compounds such as triethylsilane and tetramethyldisiloxane; metal borohydride salts such as sodium borohydride, lithium borohydride, potassium borohydride, calcium borohydride and magnesium borohydride; hydrogen and the like. Of these, metal borohydride salts such as sodium borohydride, lithium borohydride, potassium borohydride, calcium borohydride and magnesium borohydride are preferable, and alkali metal borohydride salts such as sodium borohydride, lithium borohydride and potassium borohydride are more preferable in terms of reactivity in the case of combination with a titanium compound and industrially inexpensive availability.

The amount of the reducing agent and the titanium compound used in the step (b) is nor particularly limited, and can be appropriately adjusted in view of the reactivity of the compound (2) and the like. The amount of the reducing agent used is preferably in a range of 0.5 to 5.0 equivalents, more preferably in a range of 0.5 to 3.0 equivalents, and still more preferably in a range of 0.5 to 2.0 equivalents based on 1 equivalent of the compound (2). Such amount of the reducing agent used is suitable in terms of producing the target compound (1) in a high purity and/or a high yield. The amount of the titanium compound used is preferably in a range of 0.05 to 5.0 equivalents, more preferably in a range of 0.1 to 3.0 equivalents, and still more preferably in a range of 0.5 to 2.0 equivalents based on 1 equivalent of the compound (2). Such amount of the titanium compound used is suitable in terms of producing the compound (1) in a high yield.

A solvent used in the step (b) is preferably a solvent suitable for a reduction reaction. Examples of such solvent include acetonitrile, propionitrile, THF, 2-methyl-THF, 1,4-dioxane, t-butyl methyl ether, dimethoxyethane, diglyme, methylene chloride, chloroform, carbon tetrachloride, 1,2-dichloroethane, chlorobenzene, toluene, xylene, hexane, heptane and the like. The solvent used in the step (b) may be one solvent or a mixed solvent of two or more solvents. In terms of reactivity, the solvent used in the step (b) preferably contains one or more solvents selected from methylene chloride, THF, dimethoxyethane, diglyme and the like. When the step (a) includes a step of producing the compound (2), the same solvent as in the step (b) can be used in the step of producing the compound (2). When the same solvent as in the step (b) is used in the step of producing the compound (2), the solvent used in the step of producing the compound (2) can be used in the step (b) as it is.

The amount of the solvent used in the step (b) can be appropriately adjusted in view of the volume of a reaction container and the like. The amount of the solvent used is usually in a range of 1 to 100 parts by volume based on 1 part by mass of the compound (2).

In the step (b), the order of addition of the compound (2), the titanium compound and the reducing agent to the solvent is not particularly limited, and can be appropriately determined in view of production equipment and the like. Examples of an addition method include a method of adding the compound (2) to the solvent, followed by addition of the titanium compound and the reducing agent, a method of adding the titanium compound and the reducing agent to the solvent, followed by addition of the compound (2) and the like, but a method of adding the titanium compound and the reducing agent to the solvent, followed by addition of the compound (2) is preferable. Specifically, a method of adding the titanium compound and the reducing agent to the solvent to react the reducing agent with the titanium compound at 20 to 120° C., followed by addition of the compound (2) to the solvent is preferable in terms of a high yield of the reduction reaction. The time during which the reducing agent is reacted with the titanium compound can be appropriately adjusted in a range of 0.1 to 17 hours.

The reaction temperature of the reduction reaction of the compound (2) can be appropriately adjusted usually in a range of −30 to 120° C. The reaction time of the reduction reaction of the compound (2) can be appropriately adjusted usually in a range of 0.5 to 24 hours.

After the step (b), a post-treatment may be performed. The post-treatment is not particularly limited, and a usual reaction treatment can be applied. For example, after the step (b), water, hydrochloric acid water, etc., are added into the reaction solution to stop the reaction, followed by extraction of the product with an organic solvent such as chloroform. Then, the resultant organic layer is isolated through separation and concentrated, followed by purification by silica gel column chromatography, etc., thus enabling isolation of the compound (1).

Examples of reaction schemes in the step (b) include the following reaction schemes.

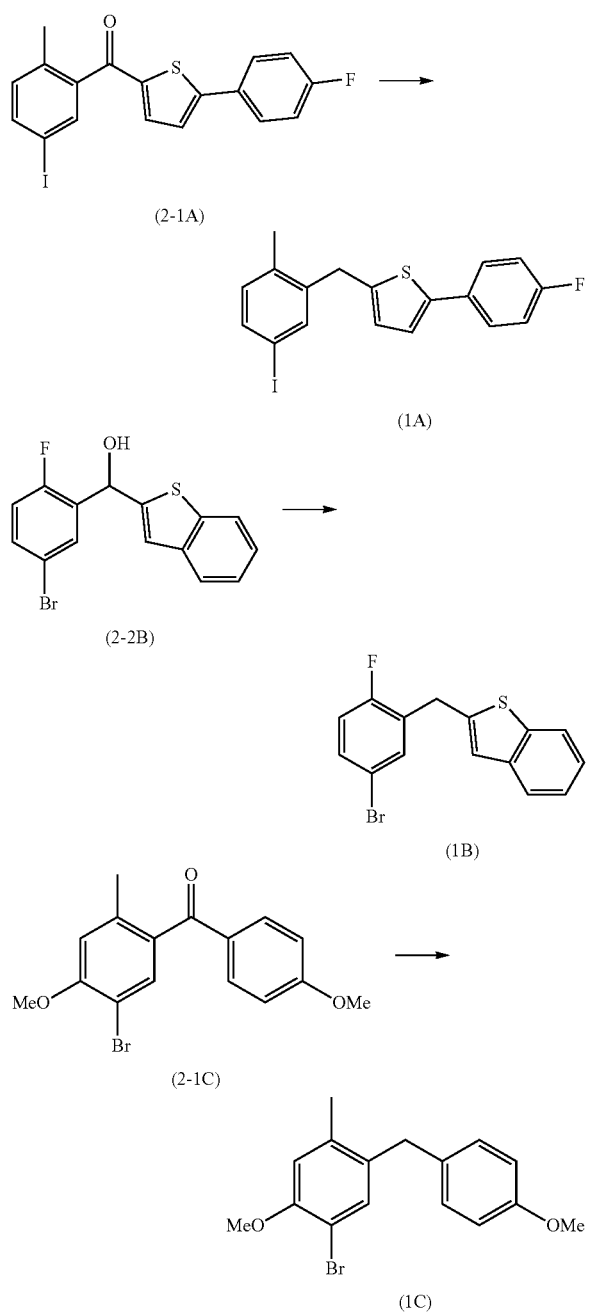

(2-1A)

(1A)

(2-2B)

(1B)

(2-1C)

(1C)

<Second Aspect>

The second aspect of the present invention relates to a method for producing a compound (1), which includes the following steps (c) and (d):
(c) a step of providing a ketone compound (2-1); and
(d) a step of reducing the ketone compound (2-1) by using a reducing agent to produce the compound (1).

Step (c)

The ketone compound (2-1) to be provided in the step (c) may be an industrially and commercially available product, or may be a compound produced in the step (c).

The step (c) can include a step of producing the ketone compound (2-1). In the step of producing the ketone compound (2-1), it is possible to produce the ketone compound (2-1) by using a production method according to the third aspect of the present invention.

Step (d)

Examples of the reducing agent used in the step (d) include triethylsilane, tetramethyldisiloxane, sodium borohydride, sodium cyanoborohydride, sodium triacetoxyborohydride, hydrogen and the like. Of these reducing agents, tetramethyldisiloxane, sodium borohydride, hydrogen and the like are preferable in terms of industrially inexpensive availability. The amount of the reducing agent used may be an amount enough to make the reaction proceed, and can be appropriately adjusted usually in a range of 0.5 to 10 equivalents based on 1 equivalent of the ketone compound (2-1).

In the step (d), an additive may be used in order to accelerate the reduction reaction. Examples of such additive include a trifluoroboron-ether complex, titanium tetrachloride, trifluoroacetic acid, palladium carbon and the like. When the step (c) includes the step of producing the ketone compound (2-1) and the ketone compound (2-1) is produced by using a production step according to the third aspect of the present invention in the step of producing the ketone compound (2-1), the titanium compound such as titanium tetrachloride used in the step of producing the ketone compound (2-1) can be used as an additive for accelerating the reduction reaction in the step (d) as it is. Therefore, this is preferable in terms of the fact that after production of the ketone compound (2-1), it is possible to successively perform a reduction reaction of the ketone compound (2-1) and to effectively produce the compound (1).

A solvent used in the step (d) is preferably a solvent suitable for a reduction reaction. Examples of such solvent include acetonitrile, propionitrile, THF, 2-methyl-THF, 1,4-dioxane, t-butyl methyl ether, dimethoxyethane, diglyme, methylene chloride, chloroform, carbon tetrachloride, 1,2-dichloroethane, chlorobenzene, toluene, xylene, hexane, heptane and the like. The solvent used in the step (d) may be one solvent or a mixed solvent of two or more solvents. In terms of reactivity, the solvent used in the step (d) preferably contains one or more solvents selected from methylene chloride, THF, dimethoxyethane, diglyme and the like. When the step (c) includes the step of producing the ketone compound (2-1), the same solvent as in the step (d) can be used in the step of producing the ketone compound (2-1). When the same solvent as in the step (d) is used in the step of producing the ketone compound (2-1), the solvent used in the step of producing the ketone compound (2-1) can be used as a solvent in the step (d) as it is. The amount of the solvent used can be appropriately adjusted in view of the volume of a reaction container and the like. The amount of the solvent used is usually in a range of 1 to 100 parts by volume based on 1 part by mass of the ketone compound (2-1). The reaction temperature can be appropriately adjusted usually in a range of −30 to 120° C., and the reaction time can be appropriately adjusted usually in a range of 0.5 to 24 hours.

After the step (d), a post-treatment may be performed. The post-treatment is not particularly limited, and a usual reaction treatment can be applied. For example, after the step (d), water, hydrochloric acid water, etc., are added into the reaction solution to stop the reaction, followed by extraction of the product with an organic solvent such as chloroform. Then, the resultant organic layer is isolated through separation and concentrated, followed by purification by silica gel column chromatography, etc., thus enabling isolation of the compound (1).

<Third Aspect>

The third aspect of the present invention relates to a method for producing a compound (2), which includes a method for producing a ketone compound (2-1) (hereinafter referred to as "Aspect 3A"), a method for producing an alcohol compound (2-2) (hereinafter referred to as "Aspect 3B") and a method for producing an ether compound (2-3) (hereinafter referred to as "Aspect 3C").

<Aspect 3A>

Aspect 3A relates to a method for producing a ketone compound (2-1), which includes the following steps (e) and (f):

(e) a step of providing an acid halide compound (4) represented by the following formula (4):

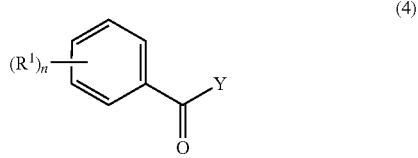

wherein $R^1$ and n are the same as defined above, and Y is a halogen atom; and (f) a step of reacting the acid halide compound (4) with an aromatic compound (5) represented by the following formula (5):

H—Ar  (5)

wherein Ar is the same as defined above,
in the presence of a titanium compound to produce the ketone compound (2-1).

Step (e)

The acid halide compound (4) to be provided in the step (e) may be an industrially and commercially available product, or may be a compound produced in the step (e).

In formula (4), $R^1$ and n are the same as in formula (1). Therefore, the above descriptions on $R^1$ and n in formula (1) are also applied to $R^1$ and n in formula (4).

In formula (4), Y is preferably a chlorine atom.

Examples of suitable compounds among the acid halide compounds (4) represented by formula (4) include the following compounds.

The step (e) can include a step of producing the acid halide compound (4).

In the step of producing the acid halide compound (4), it is possible to produce the acid halide compound (4) by reacting the corresponding carboxylic acid with a halogenating agent such as thionyl chloride, oxalyl chloride, phosphorous trichloride, thionyl bromide and phosphorus tribromide. The amount of the halogenating agent used can be appropriately adjusted according to the type of the acid halide compound (4), the type of the halogenating agent and the like. The amount of the halogenating agent used is usually in a range of 1 to 5 equivalents based on 1 equivalent of carboxylic acid. When the acid halide compound (4) is produced, an additive may be used in order to accelerate the acid halogenation reaction. Examples of the additive include dimethylformamide and the like. The amount of the additive used can be appropriately adjusted usually in a range of 0.001 to 1 equivalent based on 1 equivalent of carboxylic acid. Examples of the solvent used in the acid halogenation reaction include acetonitrile, propionitrile, THF, 2-methyl-THF, 1,4-dioxane, t-butyl methyl ether, dimethoxyethane, diglyme, methylene chloride, chloroform, carbon tetrachloride, 1,2-dichloroethane, chlorobenzene, toluene, xylene, hexane, heptane and the like. The solvent used in the acid halogenation reaction may be one solvent or a mixed solvent of two or more solvents. In terms of reactivity, it is preferably to use methylene chloride, THF, dimethoxyethane, diglyme and the like as the solvent. The amount of the solvent used can be appropriately adjusted in view of the volume of a reaction container and the like. The amount of the solvent used can be appropriately adjusted usually in a range of 1 to 100 parts by volume based on 1 part by mass of carboxylic acid. The temperature and the time of the acid halogenation can be appropriately adjusted according to the progress of the acid halogenation reaction. The temperature of the acid halogenation is usually in a range of −30 to 120° C., and the time of the acid halogenation is usually in a range of 0.1 to 10 hours.

Step (f)

In the step (f), the acid halide compound (4) is reacted with the aromatic compound (5) in the presence of a titanium compound to produce the ketone compound (2-1). The reaction occurred in the step (f) is a Friedel-Crafts acylation reaction.

In the step (f), the titanium compound acts as a Lewis acid. By using the titanium compound, it is possible to efficiency produce the ketone compound (2-1) in a high yield. In the step (f), a Lewis acid other than the titanium compound may be used in place of the titanium compound or together with the titanium compound.

The description on "titanium compound" herein is also applied to the titanium compound used in the step (f).

The aromatic compound (5) has a group represented by Ar, namely, a group selected from a substituted or unsubstituted aromatic ring group and a substituted or unsubstituted aromatic heterocyclic group. In formula (5), Ar is the same as in formula (1). Therefore, the above description on Ar in formula (1) is also applied to Ar in formula (5). The aromatic compound (5) is preferably a compound having a group selected from a substituted or unsubstituted aromatic ring group having 6 to 20 carbon atoms and a substituted or unsubstituted aromatic heterocyclic group having 6 to 20 carbon atoms. Examples of such aromatic compound include methylbenzene, methoxybenzene, dimethylaminobenzene, benzofuran, benzothiophene, 2-(4-fluorophenyl)thiophene and the like. Of these aromatic compounds, the aromatic compound (5) is particularly preferably methoxybenzene, benzothiophene, 2-(4-fluorophenyl)thiophene and the like in terms of the fact that they are useful as a synthetic intermediate for an active pharmaceutical ingredient of an antidiabetic drug or the like.

The amount of the acid halide compound (4) and the aromatic compound (5) used in the step (f) is nor particularly limited, and can be appropriately adjusted in view of the reactivity of the acid halide compound (4) and the aromatic compound (5) and the like. In terms of production of the ketone compound (2-1) in a high purity and/or a high yield, the amount of the aromatic compound (5) used is usually in a range of 1 to 100 equivalents, preferably in a range of 1 to 10 equivalents, and more preferably in a range of 1 to 2 equivalents based on 1 equivalent of the acid halide compound (4). In terms of production of the ketone compound (2-1) in a high yield, the amount of the titanium compound used is usually in a range of 0.1 to 10 equivalents, preferably in a range of 0.5 to 5 equivalents, and more preferably in a range of 1.0 to 3 equivalents based on 1 equivalent of the acid halide compound (4).

A solvent used in the step (f) can be appropriately selected from known solvents used in a Friedel-Crafts acylation reaction. Examples of such solvent include acetonitrile, propionitrile, THF, 2-methyl-THF, 1,4-dioxane, t-butyl methyl ether, dimethoxyethane, diglyme, methylene chloride, chloroform, carbon tetrachloride, 1,2-dichloroethane, chlorobenzene, toluene, xylene, hexane, heptane and the like. The solvent used in the step (f) may be one solvent or a mixed solvent of two or more solvents. In terms of reactivity and solubility, the solvent used in the step (f) preferably contains one or more solvents selected from methylene chloride, THF, dimethoxyethane and diglyme. When the step (e) includes a step of producing the acid halide compound (4), the same solvent as in the step (f) can be used in the step of producing the acid halide compound (4). When the same solvent as in the step (f) is used in the step of producing the acid halide compound (4), the solvent used in the step of producing the acid halide compound (4) can be used as a solvent in the step (f) as it is. The amount of the solvent used can be appropriately adjusted in view of the volume of a reaction container and the like. The amount of the solvent used is usually in a range of 1 to 100 parts by volume based on 1 part by mass of the acid halide compound (4). The reaction temperature can be appropriately adjusted usually in a range of −30 to 120° C., and the reaction time can be appropriately adjusted usually in a range of 0.5 to 24 hours.

After production of the ketone compound (2-1), a post-treatment may be performed. The post-treatment is not particularly limited, and a usual reaction treatment can be applied. For example, after the reaction, water, hydrochloric acid water, etc., are added into the reaction solution to stop the reaction, followed by extraction of the product with an organic solvent such as chloroform. Then, the resultant organic layer is isolated through separation and concentrated, followed by purification by silica gel column chromatography, etc., thus enabling isolation of the target ketone compound (2-1).

Examples of reaction schemes in the step (f) include the following reaction schemes.

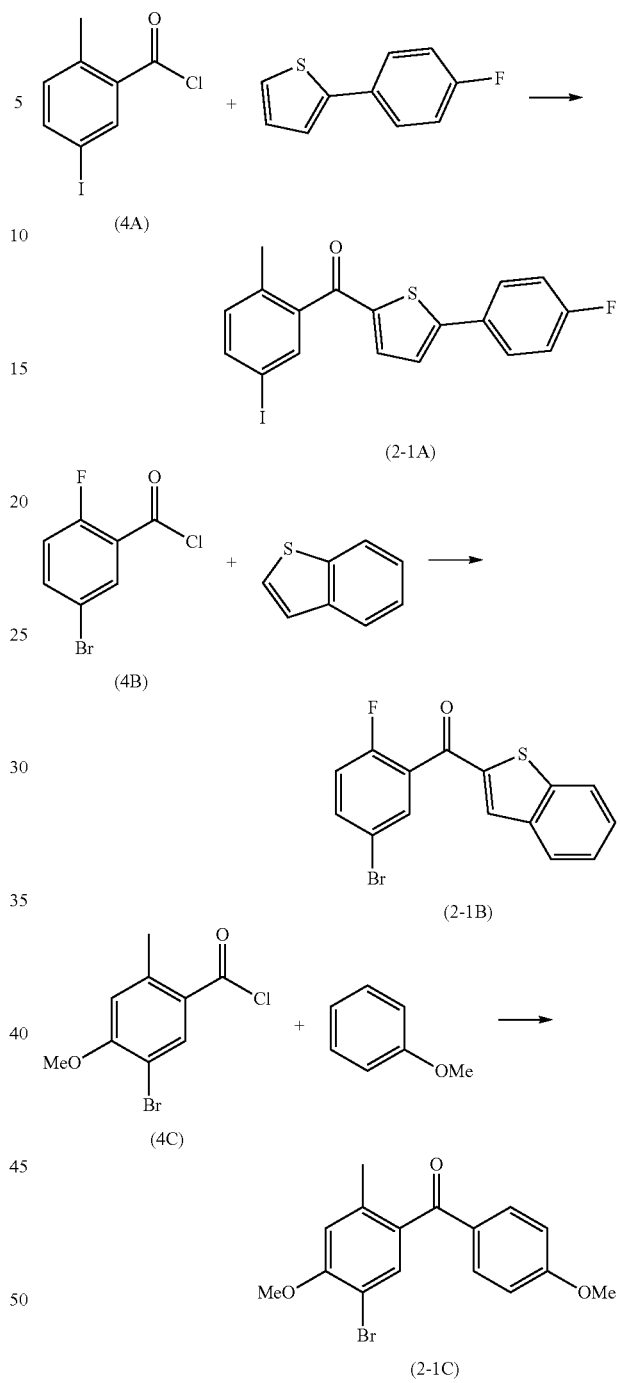

A ketone compound (2-1A) is useful as a synthetic intermediate for canagliflozin, a ketone compound (2-1B) is useful as a synthetic intermediate for ipragliflozin, and a ketone compound (2-1C) is useful as a synthetic intermediate for luseogliflozin. All of canagliflozin, ipragliflozin and luseogliflozin are antidiabetic drugs.

<Aspect 3B>

Aspect 3B relates to a method for producing an alcohol compound (2-2).

In one embodiment, a production method according to Aspect 3B includes a step of reducing the ketone compound (2-1) to produce the alcohol compound (2-2). The ketone compound (2-1) can be reduced in accordance with a conventional method.

In another embodiment, the production method according to Aspect 3B includes a step of reacting an organic metal compound (6) represented by the following formula (6):

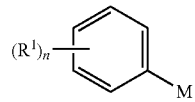
(6)

wherein $R^1$ and n are the same as defined above, and M is a metal atom or a metal halide, with an aldehyde compound (7) represented by the following formula (7):

<p style="text-align:center">OHC—Ar     (7)</p> wherein Ar is the same as defined above, to produce the alcohol compound (2-2).

In formula (6), $R^1$ and n are the same as in formula (1). Therefore, the above descriptions on $R^1$ and n in formula (1) are also applied to $R^1$ and n in formula (6).

In formula (6), M is a metal atom or a metal halide. Examples of the metal atom include lithium and the like, and examples of the metal halide include magnesium bromide, magnesium chloride, magnesium iodide and the like.

In formula (7), Ar is the same as in formula (1). Therefore, the above description on Ar in formula (1) is also applied to Ar in formula (7).

<Aspect 3C>

Aspect 3C relates to a method for producing an ether compound (2-3), which includes a step of reacting the alcohol compound (2-2) with alkanol in the presence of an acid (e.g., methanesulfonic acid, a boron fluoride-ether complex, etc.) to produce the ether compound (2-3).

EXAMPLES

Hereinafter, examples of the present invention will be described, but the present invention is not limited to these examples.

Example 1

A compound (1A) was synthesized in accordance with the following reaction formula.

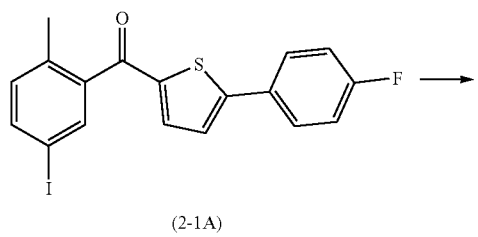
(2-1A)

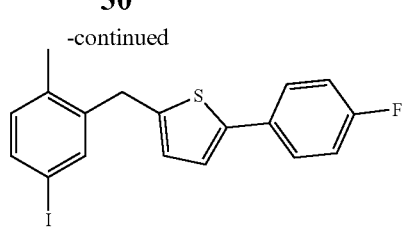
(1A)

To a dimethoxyethane (DME, 1 mL) solution of a ketone compound (2-1A) (100 mg, 0.24 mmol), sodium borohydride (9.1 mg, 0.24 mmol) was added, followed by stirring at 70° C. for 2 hours. After cooling to room temperature, a methylene chloride solution of $TiCl_4$ (133 mg, containing $TiCl_4$ (45.9 mg, 0.24 mmol)) was added over 5 minutes, followed by stirring at 50° C. for 5 hours. After allowing to stand at room temperature overnight, water (5 mL) was added to the reaction solution and the solution was stirred for 30 minutes, followed by extraction with chloroform (10 mL). The organic layer was washed with water (5 mL×2), followed by an HPLC analysis, revealing that a reductant (62.7 mg, 64%) was contained.

The above extract was concentrated under reduced pressure, and the concentrated residue was purified with a silica gel column (ethyl acetate) to obtain a compound (1A) as a crystal (56.4 mg, yield of 57.6%).

[Evaluation of Physical Property]

With respect to the compound (1A) thus obtained, various analytical results are shown below.

Melting point 109 to 110° C.

IR (KBr) 1,509 cm-1

$^1$H-NMR (CDCl$_3$) δ 2.30 (s, 3H), 4.10 (s, 2H), 6.60-7.75 (m, 9H)

[HPLC Analytical Conditions]

Sample concentration: 0.05%

Injection volume: 1.0 μL

Wavelength: 254 nm

Flow rate: 1.0 mL/min

Mobile phase: 0 to 15 min ($CH_3CN$:water=50:50 to $CH_3CN$:water=100:0)

Column temperature: 30° C.

Filler: X Bridge C18 5 μm (4.6×150 mm)

Retention time: compound (1A): 4.3 min

Example 2

To the same DME (1 mL) solution of a ketone compound (2-1A) (100 mg, 0.24 mmol) as in Example 1, sodium borohydride (14 mg, 0.37 mmol) was added, followed by stirring at 70° C. for 2 hours. After cooling to room temperature, a methylene chloride solution of $TiCl_4$ (200 mg, containing $TiCl_4$ (67 mg, 0.35 mmol)) was added over 5 minutes, followed by stirring at 50° C. for 5 hours. After allowing to stand at room temperature overnight, water (5 mL) was added to the reaction solution and the solution was stirred for 30 minutes, followed by extraction with chloroform (10 mL). The organic layer was washed with water (5 mL×2), followed by an HPLC analysis, revealing that a compound (1A) (83.7 mg, 85.4%) was contained.

Comparative Example 1

The same operations were performed as in Example 1 except that $MgCl_2$ was added in place of $TiCl_4$, but no reaction proceeded at all.

Comparative Example 2

The same operations were performed as in Example 1 except that $H_2SO_4$ was added in place of $TiCl_4$, but no reaction proceeded at all.

Comparative Example 3

The same operations were performed as in Example 1 except that $FeCl_3$ was added in place of $TiCl_4$. As a result, no compound (1A) was obtained, but an alcohol form (49 mg, 50%, HPLC assay yield) was obtained.

The reaction solution was subjected to the same treatment as in Example 1. The resultant solution was concentrated under reduced pressure, and the concentrated residue was purified with a silica gel column (hexane/ethyl acetate=20:1) to obtain an alcohol form as a crystal (44.1 mg, yield of 45%).

[Evaluation of Physical Property]

With respect to the alcohol form thus obtained, various analytical results are shown below.

Melting point 100 to 102° C.

IR (KBr) 3,566, 1,509 $cm^{-1}$ $^1$H-NMR (CDCl$_3$) δ 2.30 (s, 3H), 2.40-2.50 (m, 1H), 6.10-6.20 (m, 1H), 6.60-8.10 (m, 9H)

Example 3

A compound (1A) was synthesized in accordance with the following reaction formula.

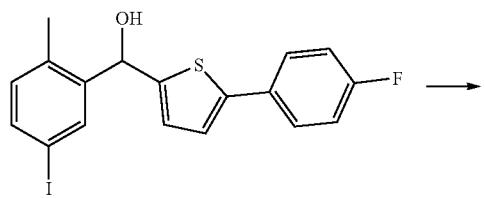

(2-2A)

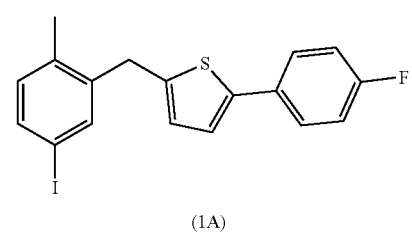

(1A)

To a DME (1 mL) solution of sodium borohydride (13 mg, 0.34 mmol), a methylene chloride solution (180 mg) of $TiCl_4$ (67 mg, 0.35 mmol) was slowly added, followed by stirring at 50° C. for 1 hour. To this reaction solution, an alcohol compound (2-2A) (50 mg, 0.12 mmol) was added, followed by stirring at 50° C. for 3 hours. Water (5 mL) was added to the reaction solution and the solution was stirred for 30 minutes, followed by extraction with ethyl acetate (3 mL) and an HPLC analysis, revealing that 33.5 mg (68.4%) of a reductant (1A) was contained.

Example 4

A ketone compound (2-1A) was synthesized in accordance with the following reaction formula.

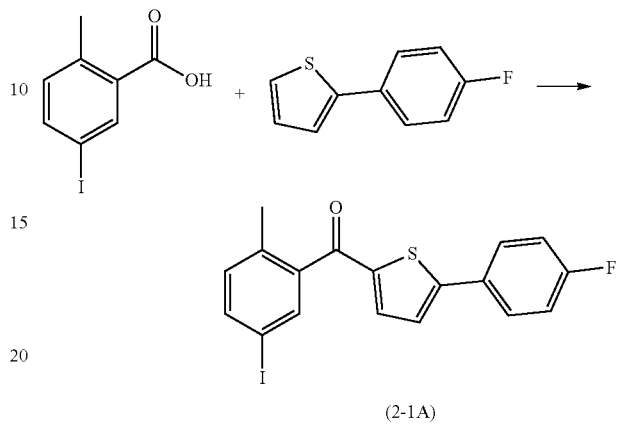

(2-1A)

To a dichloromethane (1 mL) solution of 5-iodotoluic acid (0.30 g, 1.14 mmol), DMF (0.004 g, 0.05 mmol) and thionyl chloride (0.28 g, 2.35 mmol) were sequentially added, followed by stirring at 50° C. for 1 hour. The reaction solution was concentrated under reduced pressure, and the concentrated residue was dissolved in dichloromethane (1 mL). To this solution, a methylene chloride (1 mL) solution of titanium tetrachloride (0.33 g, 1.74 mmol) was added dropwise at 6° C. over 1 minute, followed by stirring at the same temperature for 30 minutes. To this reaction solution, 2-(4-fluorophenyl)thiophene (0.20 g, 1.12 mmol) was added over 5 minutes, and the solution was stirred at the same temperature for 30 minutes, followed by stirring at room temperature for 4 hours. To the resultant reaction solution, water (10 mL) was added, and the product was extracted with chloroform (10 mL×2). The resultant organic layer was combined, followed by an HPLC analysis, revealing that a ketone compound (2-1A) (433 mg, 91.7%) was contained.

This solution was concentrated under reduced pressure, and the resultant crude crystal was recrystallized from a mixed solution of ethyl acetate and hexane to obtain a ketone compound (2-1A) (390 mg, yield of 82.5%) as a crystal.

[Evaluation of Physical Property]

With respect to the ketone compound (2-1A) thus obtained, various analytical results are shown below.

Melting point 127 to 129° C.

IR (KBr) 1,625, 1,597 $cm^{-1}$ $^1$H-NMR (CDCl$_3$) δ 2.35 (s, 3H), 7.00-8.00 (m, 9H)

[HPLC Analytical Conditions]

Sample concentration: 0.05%

Injection volume: 1.0 μL

Wavelength: 254 nm

Flow rate: 1.0 mL/min

Mobile phase: 0 to 15 min ($CH_3CN$:water=50:50 to $CH_3CN$:water=100:0)

Column temperature: 30° C.

Filler: X Bridge C18 5 μm (4.6×150 mm)

Retention time: ketone compound: 12.96 min

Example 5

A ketone compound (2-1D) was synthesized in accordance with the following reaction formula.

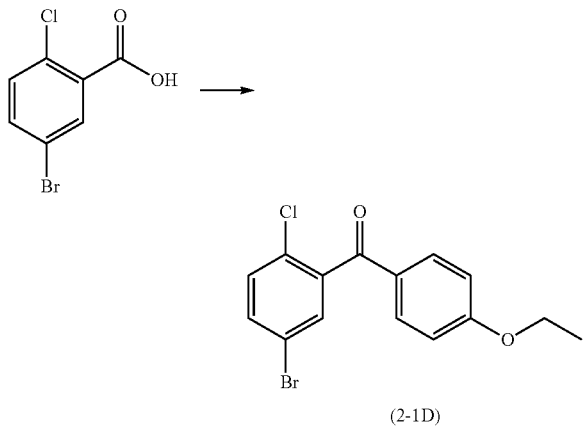

(2-1D)

To a chloroform (50 ml) solution of 5-bromo-2-chlorobenzoic acid (5.00 g, 21.2 mmol), DMF (0.015 g, 0.2 mmol) was added, followed by cooling to 10° C. Then, oxalyl chloride (2.96 g, 23.3 mmol) was added, followed by stirring at the same temperature for 10 minutes and at 20 to 25° C. for 20 hours. After the reaction solution was concentrated under reduced pressure, methylene chloride (20 mL) was added, followed by cooling with ice water to 10° C. To this solution, a methylene chloride (20 ml) solution of titanium(IV) tetrachloride (6.04 g, 31.8 mmol) was added dropwise over 3 minutes. After stirring at 8 to 10° C. for 15 minutes, phenetole (2.59 g, 21.2 mmol) was added dropwise at the same temperature over 15 minutes. After stirring at 8 to 10° C. for 3 hours, water (20 mL) was added to the reaction solution and the liquid was separated, followed by extraction of the aqueous layer with methylene chloride (20 mL). The organic layer was combined, washed with water (20 mL), and dehydrated over magnesium sulfate, followed by filtration and concentration under reduced pressure. The concentrated residue was purified with a silica gel column (elution solvent: ethyl acetate) to obtain a ketone compound (2-1D) (6.87 g, yield: 95.3%).

The invention claimed is:

1. A method for producing a compound (1A) represented by the following formula (1A):

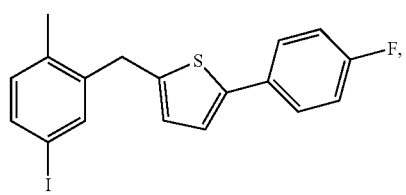

(1A)

the method comprising the following steps (a) and (b):
(a) a step of providing a compound (2-1A) represented by the following formula (2-1A):

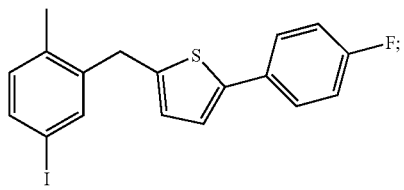

(2-1A)

and
(b) a step of reducing the compound (2-1A) in the presence of $TiCl_4$ by using an alkali metal borohydride salt to produce the compound (1A).

2. The production method according to claim 1, wherein in the step (b), $TiCl_4$ and the alkali metal borohydride salt are added to a solvent to react the alkali metal borohydride salt with $TiCl_4$ at 20 to 120° C., followed by addition of the compound (2-1A) to the solvent.

3. A method for producing a compound (1A) represented by the following formula (1A):

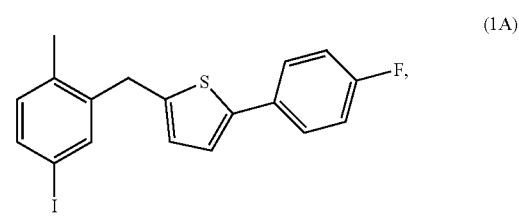 [SMILES: Cc1ccc(I)cc1Cc1ccc(-c2ccc(F)cc2)s1]

(1A)

the method comprising the following steps (a) and (b):
(a) a step of providing a compound (2-1A) represented by the following formula (2-1A):

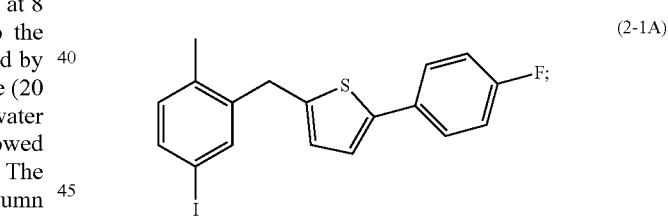

(2-1A)

and
(b) a step of reducing the compound (2-1A) in the presence of a titanium compound by using an alkali metal borohydride salt to produce the compound (1A), wherein:
the step (a) comprises a step of reacting a compound (4A) represented by the following formula (4A):

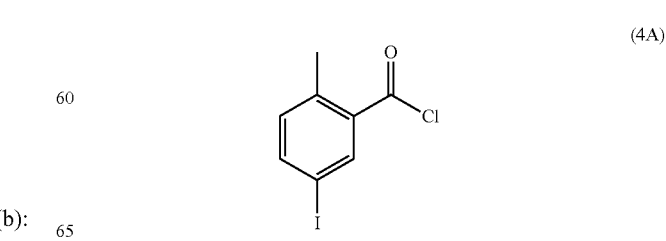

(4A)

with a compound (5) represented by the following formula (5):

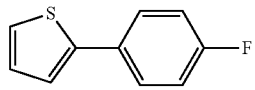 (5)

in the presence of a titanium compound to produce the compound (2-1A).

4. The production method according to claim 3, wherein the titanium compound used in the step (b) is a titanium salt represented by the following formula (3):

$$TiR^3_r(OR^4)_s \quad (3)$$

wherein
$R^3$ is a halogen atom,
$R^4$ is a substituted or unsubstituted $C_{1-6}$ alkyl group,
r and s are integers of 0 to 4 satisfying r+s=3 or 4,
or a solvate thereof.

5. The production method according to claim 3, wherein in the step (b), the titanium compound and the alkali metal borohydride salt are added to a solvent to react the alkali metal borohydride salt with the titanium compound at 20 to 120° C., followed by addition of the compound (2-1A) to the solvent.

6. The production method according to claim 3, wherein the titanium compound used in the step (a) is the titanium salt represented by formula (3) or a solvate thereof.

7. The production method according to claim 4, wherein in the step (b), the titanium compound and the alkali metal borohydride salt are added to a solvent to react the alkali metal borohydride salt with the titanium compound at 20 to 120° C., followed by addition of the compound (2-1A) to the solvent.

8. The production method according to claim 4, wherein the titanium compound used in the step (a) is the titanium salt represented by formula (3) or a solvate thereof.

9. The production method according to claim 5, wherein the titanium compound used in the step (a) is the titanium salt represented by formula (3) or a solvate thereof.

10. The production method according to claim 7, wherein the titanium compound used in the step (a) is the titanium salt represented by formula (3) or a solvate thereof.

* * * * *